(12) United States Patent
Yang et al.

(10) Patent No.: US 11,827,697 B2
(45) Date of Patent: Nov. 28, 2023

(54) ANTI-PD-1/ANTI-VEGF NATURAL ANTIBODY STRUCTURE LIKE HETERODIMERIC FORM BISPECIFIC ANTIBODY AND PREPARATION THEREOF

(71) Applicant: BEIJING HANMI PHARMACEUTICAL CO., LTD., Beijing (CN)

(72) Inventors: Yaping Yang, Beijing (CN); Nanmeng Song, Beijing (CN); Wenchu Xiao, Beijing (CN); Zhenlei Li, Beijing (CN); Lina Zhang, Beijing (CN); Mingyue Gu, Beijing (CN); Chunguang Zhan, Beijing (CN); Jiawang Liu, Beijing (CN); Maengsup Kim, Beijing (CN)

(73) Assignee: Beijing Hanmi Pharmaceutical Co., Ltd., Beijing (CN)

( * ) Notice: Subject to any disclaimer, the term of this patent is extended or adjusted under 35 U.S.C. 154(b) by 456 days.

(21) Appl. No.: 16/968,677

(22) PCT Filed: Feb. 2, 2019

(86) PCT No.: PCT/CN2019/074541
§ 371 (c)(1),
(2) Date: Aug. 10, 2020

(87) PCT Pub. No.: WO2019/154349
PCT Pub. Date: Aug. 15, 2019

(65) Prior Publication Data
US 2021/0040193 A1   Feb. 11, 2021

(30) Foreign Application Priority Data

Feb. 11, 2018   (CN) ......................... 201810141323.0

(51) Int. Cl.
| | |
|---|---|
| C07K 16/22 | (2006.01) |
| C07K 16/28 | (2006.01) |
| C07K 16/32 | (2006.01) |
| A61P 35/00 | (2006.01) |
| A61K 39/00 | (2006.01) |

(52) U.S. Cl.
CPC .............. *C07K 16/22* (2013.01); *A61P 35/00* (2018.01); *C07K 16/2818* (2013.01); *C07K 16/32* (2013.01); *A61K 2039/505* (2013.01); *C07K 2317/14* (2013.01); *C07K 2317/31* (2013.01); *C07K 2317/52* (2013.01); *C07K 2317/55* (2013.01); *C07K 2317/569* (2013.01); *C07K 2317/76* (2013.01)

(58) Field of Classification Search
None
See application file for complete search history.

(56) References Cited

U.S. PATENT DOCUMENTS

| | | |
|---|---|---|
| 5,731,168 A | 3/1998 | Carter et al. |
| 9,562,109 B2 | 2/2017 | Von Kreudenstein et al. |
| 9,988,460 B2 | 6/2018 | Von Kreudenstein et al. |
| 11,168,149 B2 * | 11/2021 | Xu .......................... C12N 15/62 |
| 2006/0074225 A1 | 4/2006 | Chamberlain et al. |
| 2006/0280747 A1 | 12/2006 | Fuh et al. |
| 2013/0178605 A1 | 7/2013 | Blein et al. |
| 2013/0195849 A1 * | 8/2013 | Spreter Von Kreudenstein .......... C07K 16/46 530/387.3 |
| 2013/0336973 A1 | 12/2013 | Spreter Von Kreudenstein et al. |
| 2013/0336981 A1 * | 12/2013 | de Kruif ............... C07K 16/283 435/69.6 |

FOREIGN PATENT DOCUMENTS

| | | | |
|---|---|---|---|
| CN | 103429620 A | 12/2013 | |
| CN | 104080811 A | 10/2014 | |
| CN | 105111314 A | 12/2015 | |
| CN | 105175545 A | 12/2015 | |
| CN | 105175545 A * | 12/2015 | |
| CN | 107446048 A | 12/2017 | |
| JP | 2015522525 A | 8/2015 | |
| WO | 2009089004 A1 | 7/2009 | |
| WO | 2012058768 A1 | 5/2012 | |
| WO | 2012131555 A2 | 10/2012 | |
| WO | 2013060867 A2 | 5/2013 | |
| WO | 2013063702 A1 | 5/2013 | |
| WO | WO-2013060867 A2 * | 5/2013 | ........... C07K 1/1133 |
| WO | 2013166594 A1 | 11/2013 | |
| WO | 2016057933 A1 | 4/2016 | |
| WO | 2016170039 A1 | 10/2016 | |
| WO | 2017079112 A1 | 5/2017 | |

(Continued)

OTHER PUBLICATIONS

Chinese Office Action for Chinese Application No. 201980012499.9, dated Nov. 2, 2022 with translation, 15 pages.
Japanese Notice of Reasons for Refusal for Japanese Application No. 2020-542762, dated Dec. 12, 2022 with translation, 12 pages.
Afreen et al., "The Immunoinhibitory B7-H1 Molecule as a Potential Target in Cancer: Killing Many Birds with One Stone", Hematol. Oncol. Stem Cell Ther., 7(1), First Quarter 2014, 17 pages.

(Continued)

*Primary Examiner* — Misook Yu
*Assistant Examiner* — Sarah A Alsomairy
(74) *Attorney, Agent, or Firm* — RatnerPrestia

(57) ABSTRACT

An anti-PD-1/anti-VEGF natural antibody structure-like heterodimeric form bispecific antibody and preparation thereof. Provided are a highly stable, heterodimeric form anti-PD-1/anti-VEGF bispecific antibody having natural IgG characteristics and free of mismatched heavy and light chains and preparation method for the antibody. The bispecific antibody is capable of simultaneously binding with two target molecules and provides improved efficacy in treating a complicated disease.

24 Claims, 8 Drawing Sheets

Specification includes a Sequence Listing.

(56) References Cited

FOREIGN PATENT DOCUMENTS

| WO | 2017101828 A1 | 6/2017 | |
|---|---|---|---|
| WO | 2017117179 A1 | 7/2017 | |
| WO | 2017117202 A1 | 7/2017 | |
| WO | WO-2017117179 A1 * | 7/2017 | ............... A61P 35/00 |
| WO | 2018059502 A1 | 4/2018 | |

OTHER PUBLICATIONS

Brekken et al., "Selective Inhibition of Vascular Endothelial Growth Factor (VEGF) Receptor 2 (KDR/Flk-1) Activity by a Monoclonal Anti-VEGF Antibody Blocks Tumor Growth in Mice", Cancer Research, 60, Sep. 15, 2000, pp. 5117-5124.
Bruns et al., "Effect of the Vascular Endothelial Growth Factor Receptor-2 Antibody DC101 Plus Gemcitabine on Growth, Metastasis and Angiogenesis of Human Pancreatic Cancer Growing Orthotopically in Nude Mice", Int. J. Cancer, 2002, 102, 101-108.
Chen et al., "Molecular Pathways: Next Generation Immunotherapy—Inhibiting Programmed Death-Ligand 1 and Programmed Death-1", Clin. Cancer Res., Dec. 15, 2012, 18(24), 6580-7, 9 pages.
Ferrara et al., "The Biology of VEGF and its Receptors", Angiogenesis Focus, Nature Medicine, vol. 9 No. 6, Jun. 2003, pp. 669-676.
Folkman, J., "Clinical Applications of Research on Angiogenesis", New England Journal of Medicine, Seminars in Medicine of the Beth Israel Hospital, Boston, vol. 333, No. 26, Dec. 28, 1995, pp. 1757-1763.
Folkman, J., "Angiogenesis: An Organizing Principle for Drug Discovery?", Nature Reviews, Drug Discovery, vol. 6, Apr. 2007, pp. 273-286.
Gasparini et al., "Clinical Importance of the Determination of Tumor Angiogenesis in Breast Carcinoma: Much More Than a New Prognostic Tool", Journal of Clinical Oncology, vol. 13, No. 3, Mar. 1995, pp. 765-782.
Gianchecchi et al., "Recent Insights into the Role of the PD-1/PD-L1 Pathway in Immunological Tolerance and Autoimmunity", Autoimmunity Reviews 12 (2013), pp. 1091-1100.
Henick et al., "The PD-1 Pathway as a Therapeutic Target to Overcome Immune Escape Mechanisms in Cancer", Expert Opin. Ther. Targets, (2014),18(12), 14 pages.
Johnson et al., "Randomized Phase II Trial Comparing Bevacizumab Plus Carboplatin and Paclitaxel With Carboplatin and Paclitaxel Alone in Previously Untreated Locally Advanced or Metastatic Non-Small-Cell Lung Cancer", Journal of Clinical Oncology, vol. 22, No. 11, Jun. 1, 2004, pp. 2184-2191.
Kabbinavar et al., "Phase II, Randomized Trial Comparing Bevacizumab Plus Fluorouracil (FU)/Leucovorin (LV) With FU/LV Alone in Patients with Metastatic Colorectal Cancer", J. Clin. Oncol., vol. 21, No. 1, Jan. 1, 2003, pp. 60-65.

Kim et al., "Prospects for Targeting PD-1 and PD-L1 in Various Tumor Types", Oncology Journal, Nov. 11, 2014, vol. 28, Issue 11, 12 pages.
Kumar et al., "Breast Carcinoma: Vascular Density Determined Using CD105 Antibody Correlates with Tumor Prognosis", Cancer Research, 59, Feb. 15, 1999, pp. 856-861.
Lui et al., "Fc Engineering for Developing Therapeutic Bispecific Antibodies and Novel Scaffolds", Frontiers in Immunology, Jan. 2017, vol. 8, Article 38, 15 pages.
Mellman, I., "The Renaissance of Immunotherapy is a Revolution for Cancer Patients", ASCO, GU 2015, 29 pages.
Mentlik-James et al., "Combination Immune Therapies to Enhance Anti-tumor Responses by NK Cells", Frontiers in Immunology, Dec. 23, 2013, vol. 4, Article 481, 13 pages.
Motz et al., "Deciphering and Reversing Tumor Immune Suppression", Immunity 39, Jul. 25, 2013, pp. 61-73.
Ohaegbulam et al., "Human Cancer Immunotherapy with Antibodies to the PD-1 and PD-L1 Pathway", Trends in Molecular Medicine, Jan. 2015, vol. 21, No. 1, pp. 24-33.
Pardoll, D., "The Blockade of Immune Checkpoints in Cancer Immunotherapy", Nature, Apr. 2012, vol. 12(4), pp. 252-264.
Pilotto et al., "Immune Checkpoint Inhibitors for Non-small-cell Lung Cancer: Does that Represent a 'New Frontier'?", Anti-Cancer Agents in Medicinal Chemistry, 2015, vol. 15, No. 0, 7 pages.
Postow et al., "Immune Checkpoint Blockade in Cancer Therapy", Journal of Clinical Oncology, vol. 33, No. 17, Jun. 10, 2015, pp. 1974-1982 (10 pages).
Shaheen et al., "Inhibited Growth of Colon Cancer Carcinomatosis by Antibodies to Vascular Endothelial and Epidermal Growth Factor Receptors", British Journal of Cancer, (2001), 85(4), pp. 584-589.
Tartour et al., "Angiogenesis and Immunity: A Bidirectional Link Potentially Relevant for the Monitoring of Antiangiogenic Therapy and the Development of Novel Therapeutic Combination with Immunotherapy", Cancer Metastasis Rev., (2011), 30, pp. 83-95.
Tischer et al., "The Human Gene for Vascular Endothelial Growth Factor", The Journal of Biological Chemistry, vol. 266, No. 18, Jun. 25, 1991, pp. 11947-11954.
Yasuda et al., "Simultaneous Blockade of Programmed Death 1 and Vascular Endothelial Growth Factor Receptor 2 (VEGFR2) Induces Synergistic Anti-tumour Effect In Vivo", British Society for Immunology, Clinical and Experimental Immunology, 2013, 172, pp. 500-506.
International Search Report and Written Opinion for International Application PCT/CN2019/074541, dated Apr. 30, 2019, 24 pages.
Spreter Von Kreudenstein et al., "Improving Biophysical Properties of a Bispecific Antibody to Aid Developability: Quality by Molecular Design", MABS, 2013, vol. 5, No. 5, pp. 646-654.
Extended European Search Report for European Application No. 19750554.8, dated Oct. 7, 2021, 16 pages.

* cited by examiner

1. Molecular weight marker
2. The mixture of the anti-VEGF, the anti-PD-1 half antibody molecules after oxidation Figure 8 (continued 2)

SEQUENCE LISTING

```
<160> NUMBER OF SEQ ID NOS: 22

<210> SEQ ID NO 1
<211> LENGTH: 321
<212> TYPE: DNA
<213> ORGANISM: Artificial
<220> FEATURE:
<223> OTHER INFORMATION: Light chain variable region of anti-human VEGF
      antibody

<400> SEQUENCE: 1
gacatccaga tgacccagtc cccttcctcc ctgtccgctt ccgtgggcga cagggtgacc        60
atcacctgca gcgccagcca ggacatctcc aactacctga actggtatca acagaagccc       120
ggcaaggccc ccaaggtgct gatctacttc acctcctccc tgcactccgg cgtgccttcc       180
aggttttccg gctccggctc cggcacagac ttcacactga caatctcctc cctgcagcct       240
gaggacttcg ccacctacta ctgtcagcag tactccacag tgccctggac cttcggccag       300
ggcaccaagg tggagatcaa g                                                 321

<210> SEQ ID NO 2
<211> LENGTH: 107
<212> TYPE: PRT
<213> ORGANISM: Artificial
<220> FEATURE:
<223> OTHER INFORMATION: Light chain variable region of anti-human VEGF
      antibody
```

<400> SEQUENCE: 2

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys
            100                 105

<210> SEQ ID NO 3
<211> LENGTH: 321
<212> TYPE: DNA
<213> ORGANISM: Artificial
<220> FEATURE:
<223> OTHER INFORMATION: Light chain constant region of anti-human VEGF
      antibody

<400> SEQUENCE: 3
cgaactgtgg ccgctccaag cgtcttcatt tttccaccct ctgacgaaca gctgaagtca      60
gggacagctt ccgtggtctg tctgctgaac aattttttacc ccagggaggc caaagtgcag    120
tggaaggtcg ataacgctct gcagagcgga aattctcagg agagtgtgac agaacaggac    180
tcaaaagatt ccacttatag cctgtctagt accctgacac tgtccaaggc agactacgaa    240
aagcataaag tgtatgcctg tgaggtcaca catcagggtc tgtcaagccc cgtcactaag    300
tccttcaatc gtggcgaatg c                                              321

<210> SEQ ID NO 4
<211> LENGTH: 107
<212> TYPE: PRT
<213> ORGANISM: Artificial
<220> FEATURE:
<223> OTHER INFORMATION: Light chain constant region of anti-human VEGF
      antibody

<400> SEQUENCE: 4

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 5
<211> LENGTH: 369
<212> TYPE: DNA
<213> ORGANISM: Artificial
<220> FEATURE:
<223> OTHER INFORMATION: Heavy chain variable region of anti-human VEGF antibody

<400> SEQUENCE: 5

```
gaggtgcagc tggtggagtc cggaggaggc ctggtgcagc tggaggttc tctgaggctg      60
tcctgtgccg cctccggcta caccttcacc aactacggca tgaactgggt gaggcaggcc    120
cctggaaagg gcctggaatg ggtgggctgg atcaacacct acaccggcga gcccacctat    180
gccgccgact tcaagaggag gttcaccttc tccctcgaca cctccaagag caccgcctac    240
ctgcagatga actccctgag ggctgaggac accgccgtgt actactgcgc caagtacccc    300
cactactacg gctcctccca ttggtacttc gacgtgtggg gccagggcac cctggtgaca    360
gtgtcctcc                                                            369
```

<210> SEQ ID NO 6
<211> LENGTH: 123
<212> TYPE: PRT
<213> ORGANISM: Artificial
<220> FEATURE:
<223> OTHER INFORMATION: Heavy chain variable region of anti-human VEGF antibody

<400> SEQUENCE: 6

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro His Tyr Tyr Gly Ser Ser His Trp Tyr Phe Asp Val
            100                 105                 110

Trp Gly Gln Gly Thr Leu Val Thr Val Ser Ser
        115                 120
```

<210> SEQ ID NO 7
<211> LENGTH: 321
<212> TYPE: DNA
<213> ORGANISM: Artificial
<220> FEATURE:
<223> OTHER INFORMATION: Light chain variable region of anti-human VEGF antibody

<400> SEQUENCE: 7

```
gacatccaga tgacacagag ccctagcagc ctgtccgcca gcgtgggcga cagagtgacc      60
atcacctgca gagcctccca ggacgtgagc acagccgtcg cctggtatca acagaagccc    120
ggcaaggccc ccaagctgct gatctactcc gccagcttcc tgtactccgg cgtgcccagc    180
agattcagcg gcagcggaag cggcaccgac ttcaccctga ccatcagcag cctgcagccc    240
```

```
gaggacttcg ccacctacta ctgccagcag ggctacggca accccttcac cttcggccag    300
ggcaccaagg tggagatcaa g                                              321
```

<210> SEQ ID NO 8
<211> LENGTH: 107
<212> TYPE: PRT
<213> ORGANISM: Artificial
<220> FEATURE:
<223> OTHER INFORMATION: Light chain variable region of anti-human VEGF
      antibody

<400> SEQUENCE: 8

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Tyr Gly Asn Pro Phe
                85                  90                  95

Thr Phe Gly Gln Gly Thr Lys Val Glu Ile Lys
            100                 105
```

<210> SEQ ID NO 9
<211> LENGTH: 333
<212> TYPE: DNA
<213> ORGANISM: Artificial
<220> FEATURE:
<223> OTHER INFORMATION: Light chain variable region of anti-human PD-1
      antibody

<400> SEQUENCE: 9

```
gagatcgtgc tgacccagag ccctgccaca ctgagcctga gccctggcga aagggccacc    60
ctgagctgca gggctagcaa gggcgtgagc accagcggct acagctacct gcactggtat   120
caacagaagc ccggccaggc tcctaggctg ctgatctacc tggccagcta tctggagagc   180
ggcgtgcccg ctagattcag cggaagcggc agcggcaccg acttcaccct gaccatcagc   240
agcctggagc ccgaggactt cgccgtgtac tactgccagc acagcaggga cctgcctctg   300
accttcggag ccggcaccaa ggtggagatc aag                                333
```

<210> SEQ ID NO 10
<211> LENGTH: 111
<212> TYPE: PRT
<213> ORGANISM: Artificial
<220> FEATURE:
<223> OTHER INFORMATION: Light chain variable region of anti-human VEGF
      antibody

<400> SEQUENCE: 10

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Lys Gly Val Ser Thr Ser
            20                  25                  30

Gly Tyr Ser Tyr Leu His Trp Tyr Gln Gln Lys Pro Gly Gln Ala Pro
        35                  40                  45
```

```
Arg Leu Leu Ile Tyr Leu Ala Ser Tyr Leu Glu Ser Gly Val Pro Ala
        50                  55                  60
Arg Phe Ser Gly Ser Gly Ser Gly Thr Asp Phe Thr Leu Thr Ile Ser
 65                  70                  75                  80
Ser Leu Glu Pro Glu Asp Phe Ala Val Tyr Tyr Cys Gln His Ser Arg
                85                  90                  95
Asp Leu Pro Leu Thr Phe Gly Gly Gly Thr Lys Val Glu Ile Lys
            100                 105                 110
```

<210> SEQ ID NO 11
<211> LENGTH: 360
<212> TYPE: DNA
<213> ORGANISM: Artificial
<220> FEATURE:
<223> OTHER INFORMATION: Heavy chain variable region of anti-human PD-1
      antibody

<400> SEQUENCE: 11

```
caggtgcagc tggtgcagag cggcgtggag gtgaagaagc ctggcgccag cgtgaaggtg      60
agctgcaagg ccagcggcta caccttcacc aactactaca tgtactgggt gaggcaggcc     120
cctggccaag actggagtg gatgggcggc atcaaccca gcaacggcgg caccaacttc      180
aacgagaagt tcaagaacag ggtgaccctg accaccgaca gcagcaccac caccgcctac     240
atggagctga agagcctgca gttcgacgac accgccgtgt actactgcgc caggagggac     300
tacaggttcg acatgggctt cgactactgg ggccagggca ccacagtgac cgtgtccagc    360
```

<210> SEQ ID NO 12
<211> LENGTH: 120
<212> TYPE: PRT
<213> ORGANISM: Artificial
<220> FEATURE:
<223> OTHER INFORMATION: Heavy chain variable region of anti-human PD-1
      antibody

<400> SEQUENCE: 12

```
Gln Val Gln Leu Val Gln Ser Gly Val Glu Val Lys Lys Pro Gly Ala
 1               5                  10                  15
Ser Val Lys Val Ser Cys Lys Ala Ser Gly Tyr Thr Phe Thr Asn Tyr
            20                  25                  30
Tyr Met Tyr Trp Val Arg Gln Ala Pro Gly Gln Gly Leu Glu Trp Met
        35                  40                  45
Gly Gly Ile Asn Pro Ser Asn Gly Gly Thr Asn Phe Asn Glu Lys Phe
    50                  55                  60
Lys Asn Arg Val Thr Leu Thr Thr Asp Ser Ser Thr Thr Thr Ala Tyr
 65                  70                  75                  80
Met Glu Leu Lys Ser Leu Gln Phe Asp Asp Thr Ala Val Tyr Tyr Cys
                85                  90                  95
Ala Arg Arg Asp Tyr Arg Phe Asp Met Gly Phe Asp Tyr Trp Gly Gln
            100                 105                 110
Gly Thr Thr Val Thr Val Ser Ser
        115                 120
```

<210> SEQ ID NO 13
<211> LENGTH: 990
<212> TYPE: DNA
<213> ORGANISM: Artificial
<220> FEATURE:
<223> OTHER INFORMATION: Heavy chain constant region of anti-human PD-1
      antibody

<400> SEQUENCE: 13

```
gctagcacaa aaggaccttc cgtgtttcca ctggcaccct ctagtaagag tacttcagga      60
ggaaccgcag cactgggatg tctggtgaag gactacttcc agagcccgt caccgtgtct     120
tggaacagtg gagcactgac ctccggggtc catacatttc ctgccgtgct gcagtcatcc    180
ggtctgtata gcctgagctc tgtggtcaca gtcccaagtt catccctggg cacccagaca    240
tacatctgca acgtgaatca caaaccttcc aatactaagg tcgacaagaa agtgaaccc     300
aagtcctgcg ataagaccca cacatgccct ccctgtcctg ctcccgaact gctgggagga    360
ccctccgtct tcctgttccc ccccaagccc aaagacacac tgatgatcag caggaccct    420
gaagtgacct gcgtggtcgt ggacgtgagc cacgaggacc ccgaggtcaa gtttaactgg    480
tacgtggacg gcgtggaggt ccacaacgcc aagaccaagc caggagga gcagtacgcc     540
agcacctaca gggtcgtgtc cgtgctgacc gtgctccacc aagattggct caacggcaag    600
gagtataagt gcaaagtcag caacaaggcc ctccccgccc catcgagaa aaccatcagc    660
aaggccaagg gccaaccgcg ggaacctcaa gtgtataccc tccctcccag ccgggatgag    720
ctgaccaaga accaagtctc cctcttgtgc ctggtcaagg gattctaccc ttccgacatt    780
gccgtcgaat gggagagcaa tggccagccc gagaacaact acaagacaac ccccccgtc    840
ctgcgcagcg acggatcctt cttcctgtac tccaagctca ccgtggacaa gagccggtgg    900
caacagggca acgtgttctc ctgtagcgtg atgcacgaag ccctccacaa ccactatacc    960
cagaagagcc tgagcctcag ccccggcaaa                                     990
```

<210> SEQ ID NO 14
<211> LENGTH: 330
<212> TYPE: PRT
<213> ORGANISM: Artificial
<220> FEATURE:
<223> OTHER INFORMATION: Heavy chain constant region of anti-human PD-1 antibody

<400> SEQUENCE: 14

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175
```

```
Glu Gln Tyr Ala Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Leu Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Arg Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 15
<211> LENGTH: 321
<212> TYPE: DNA
<213> ORGANISM: Artificial
<220> FEATURE:
<223> OTHER INFORMATION: Light chain variable region of anti-human PD-1
      antibody

<400> SEQUENCE: 15
gacatcgtcc tgacccagag tcccgccacc ctgagcctga gtcccggaga aagagcaaca      60
ctgagctgcc gagccagcca gagcattagc aacaatctgc actggtacca gcagaagcca     120
ggacaggcac ctcgactgct gatcagattc gcttctcaga gtatctcagg gattccagca     180
aggttcagcg gctccgggtc tggaaccgac tttaccctga caattagctc cctggagccc     240
gaagatttcg ccgtgtattt ttgccagcag agcgataatt ggcccctgac attcggaggc     300
ggaactaaag tggaaatcaa a                                                321

<210> SEQ ID NO 16
<211> LENGTH: 107
<212> TYPE: PRT
<213> ORGANISM: Artificial
<220> FEATURE:
<223> OTHER INFORMATION: Light chain variable region of anti-human PD-1
      antibody

<400> SEQUENCE: 16

Asp Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Ile Ser Asn Asn
            20                  25                  30

Leu His Trp Tyr Gln Gln Lys Pro Gly Gln Ala Pro Arg Leu Leu Ile
        35                  40                  45

Arg Phe Ala Ser Gln Ser Ile Ser Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80
```

Glu Asp Phe Ala Val Tyr Phe Cys Gln Gln Ser Asp Asn Trp Pro Leu
                85                  90                  95

Thr Phe Gly Gly Gly Thr Lys Val Glu Ile Lys
            100                 105

<210> SEQ ID NO 17
<211> LENGTH: 351
<212> TYPE: DNA
<213> ORGANISM: Artificial
<220> FEATURE:
<223> OTHER INFORMATION: Heavy chain variable region of anti-human PD-1
      antibody

<400> SEQUENCE: 17
gaggtcaatc tggtggagag cggcggcggc ctggtgcagc ctggcggcag cctgagactg      60
agttgtgcag caagcgggtt cactttagc tcctacggaa tgagctgggt gaggcaggca     120
ccaggcaagg gactggagtg gtcgcctct atcagtggcg ggggacgcta cacctactat     180
cctgactcca tgaagggccg gttcacaatc tcaagagata cagcaagaa caatctgtat     240 ctgcagatga attctctgcg agccgaagac accgctgtgt actattgcgt ctacgaatac     300
ttttacacta tggactactg ggggcagggc actctggtga ccgtctcctc a              351

<210> SEQ ID NO 18
<211> LENGTH: 117
<212> TYPE: PRT
<213> ORGANISM: Artificial
<220> FEATURE:
<223> OTHER INFORMATION: Heavy chain variable region of anti-human PD-1
      antibody

<400> SEQUENCE: 18

Glu Val Asn Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gly Met Ser Trp Val Arg Gln Ala Pro Gly Lys Gly Leu Glu Trp Val
        35                  40                  45

Ala Ser Ile Ser Gly Gly Gly Arg Tyr Thr Tyr Tyr Pro Asp Ser Met
    50                  55                  60

Lys Gly Arg Phe Thr Ile Ser Arg Asp Asn Ser Lys Asn Asn Leu Tyr
65                  70                  75                  80

Leu Gln Met Asn Ser Leu Arg Ala Glu Asp Thr Ala Val Tyr Tyr Cys
                85                  90                  95

Val Tyr Glu Tyr Phe Tyr Thr Met Asp Tyr Trp Gly Gln Gly Thr Leu
            100                 105                 110

Val Thr Val Ser Ser
        115

<210> SEQ ID NO 19
<211> LENGTH: 990
<212> TYPE: DNA
<213> ORGANISM: Artificial
<220> FEATURE:
<223> OTHER INFORMATION: Heavy chain constant region of anti-human PD-1
      antibody

<400> SEQUENCE: 19
gctagcacaa aaggaccttc cgtgtttcca ctggcaccct ctagtaagag tacttcagga      60
ggaaccgcag cactgggatg tctggtgaag gactacttcc cagagcccgt caccgtgtct    120

```
tggaacagtg gagcactgac ctccggggtc catacatttc ctgccgtgct gcagtcatcc    180
ggtctgtata gcctgagctc tgtggtcaca gtcccaagtt catccctggg cacccagaca    240
tacatctgca acgtgaatca caaaccttcc aatactaagg tcgacaagaa agtggaaccc    300
aagtcctgcg ataagaccca cacatgccct cctgtcctg ctcccgaact gctgggagga    360
ccctccgtct tcctgttccc ccccaagccc aaagacacac tgatgatcag caggaccct    420
gaagtgacct gcgtggtcgt ggacgtgagc acgaggacc ccgaggtcaa gtttaactgg    480
tacgtggacg gcgtggaggt ccacaacgcc aagaccaagc caggagga gcagtacgcc    540
agcacctaca gggtggtcag cgtgctgacc gtgctgcacc aggattggct caacggcaag    600
gagtacaagt gcaaagtctc caacaaggcc ctgcccgccc ccatcgagaa gaccatctcc    660
aaggctaagg acagcccag ggagcccaa gtgtacaccg agcctcccag ccgggatgag    720
ctgaccaaga accaagtctc cctcacctgc ctggtcaagg gattctaccc ttccgacatt    780
gccgtcgaat gggagagcaa tggccagccc gagaacaact acaagacaac cccccccgtc    840
ctggatagcg acggatcctt cttcctgctc tccgtgctca ccgtcgacaa gagcagatgg    900
cagcagggca acgtgttcag ctgtagcgtg atgcacgagg ccctgcacaa ccactacacc    960
cagaagagcc tgtccctcag ccccggcaag                                    990
```

<210> SEQ ID NO 20  
<211> LENGTH: 330  
<212> TYPE: PRT  
<213> ORGANISM: Artificial  
<220> FEATURE:  
<223> OTHER INFORMATION: Heavy chain constant region of anti-human PD-1
      antibody

<400> SEQUENCE: 20

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Ala Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
```

-continued

```
                195                 200                 205
Lys Ala Leu Pro Ala Pro Ile Glu Lys Thr Ile Ser Lys Ala Lys Gly
    210                 215                 220

Gln Pro Arg Glu Pro Gln Val Tyr Thr Glu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Leu Ser Val Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 21
<211> LENGTH: 360
<212> TYPE: DNA
<213> ORGANISM: Artificial
<220> FEATURE:
<223> OTHER INFORMATION: Heavy chain variable region of anti-human VEGF antibody

<400> SEQUENCE: 21

```
gaggtgcagc tggtggagag cggaggcgga ctggtgcaac tggcggatc cctgagactg     60
agctgtgccg ccagcggctt caccatctcc gactactgga tccactgggt gaggcaggcc    120
cctggaaagg gcctggaatg ggtggccgga atcacccctg ccggcggcta cctactac     180
gccgacagcg tgaagggcag gttcaccatc agcgccgaca ccagcaagaa caccgcctac    240
ctgcagatga acagcctgag ggccgaggac accgccgtgt actactgcgc caggttcgtg    300
ttcttcctgc cctacgccat ggactactgg ggccagggaa ccctggtgac cgtgagcagc    360
```

<210> SEQ ID NO 22
<211> LENGTH: 120
<212> TYPE: PRT
<213> ORGANISM: Artificial
<220> FEATURE:
<223> OTHER INFORMATION: Heavy chain variable region of anti-human VEGF antibody

<400> SEQUENCE: 22

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Ile Ser Asp Tyr
            20                  25                  30

Trp Ile His Trp Val Arg Gln Ala Pro Gly Lys Gly Leu Glu Trp Val
        35                  40                  45

Ala Gly Ile Thr Pro Ala Gly Gly Tyr Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Phe Val Phe Phe Leu Pro Tyr Ala Met Asp Tyr Trp Gly Gln
```

```
                    100                 105                 110
Gly Thr Leu Val Thr Val Ser Ser
            115                 120
```

ANTI-PD-1/ANTI-VEGF NATURAL ANTIBODY STRUCTURE LIKE HETERODIMERIC FORM BISPECIFIC ANTIBODY AND PREPARATION THEREOF

CROSS REFERENCE TO RELATED APPLICATIONS

This application is a U.S. National Phase Application of PCT International Application No. PCT/CN2019/074541, filed Feb. 2, 2019, which claims benefit of priority from Chinese Patent Application No. 201810141323.0, filed Feb. 11, 2018. The contents of these applications are incorporated herein by reference.

FIELD

The present disclosure relates to an anti-PD-1/anti-VEGF natural antibody structure-like heterodimeric form bispecific antibody and preparation thereof. Specifically, the present disclosure provides a highly stable, heterodimeric form anti-PD-1/anti-VEGF bispecific antibody having natural IgG characteristics and free of mismatched heavy and light chains and preparation method for the antibody.

BACKGROUND

Monoclonal antibodies are highly specific antibodies that only act on a single antigen epitope, and have been widely used in the treatment of many diseases, such as cancer, inflammation, autoimmune diseases, and infectious diseases. However, if such therapeutic molecules are used alone, none of them can show sufficient drug efficacy due to the complexity of the disease, for example, cancer or inflammatory diseases usually involve multiple disease mediated molecular pathways and cross-action between signaling pathways. In these cases, single-target molecules cannot provide the best therapeutic effect, while molecules that block multiple targets or multiple sites of the same target at the same time can improve the therapeutic effect. Compared with combined administration of multiple single specific molecules, dual-targeted therapy using multispecific molecules such as bispecific molecules may enhance the efficacy and reduce toxic and side effects by introducing a new mechanism of action. At the same time, as a single molecule, it can simplify the development process of new drugs and it is convenient for patients and medical workers to use.

Many different forms of bispecific antibodies or bifunctional molecules have been reported in this field. For original bispecific antibodies, chemical methods were used to connect two existing IgG molecules, Fab' or F(ab')$_2$ fragments using a bifunctional coupling reagent. However, such chemically coupled bispecific antibodies have many limitations, such as the intensity of production, the complexity and low yield of purification of heterologous conjugates, removal of homologous conjugates, and original monospecific antibodies or fragments.

Another method for generating bispecific antibodies is to use the hybrid-hybridoma (or quadroma) technology, which is produced by somatic cell fusion of two hybridoma cell lines secreting different antibodies. Due to the random pairing of immunoglobulin heavy and light chains, only 1/10 of the antibody mixture is the needed functional bispecific antibody, which complicates the purification process and reduces production yield.

WO2013060867 describes a method for large-scale production of heterodimeric bispecific antibodies. This method first reduces two mixed homodimeric form antibodies, then introduce asymmetric amino acid mutations in the CH3 region of these two homodimeric antibodies thereby promoting the exchange of Fab arms of different antibodies, and then form stable bispecific antibodies by oxidizing the interchain disulfide bonds in the hinge region.

WO2009089004 describes a method for preparing heterodimeric protein by mutating the amino acid at the CH3-CH3 interface to a charged amino acid, thereby promoting the formation of heterodimer by electrostatic force while hindering homodimer formation.

U.S. Pat. No. 5,731,168 describes a method for preparing heterodimeric IgG using a "protuberance-into-cavity" strategy. The method replaces small amino acids from the interface of the CH3 region of the first chain with larger amino acids and thereby forming the "protuberance"; at the same time, it mutates large amino acids into smaller ones on the CH3 interface of the second chain and thereby forming the "cavity". The interaction of the "protuberance" and the "cavity" favors heteromultimer formation, instead of homomultimer formation.

WO2012058768 describes a method for making a stable and highly specific heterodimeric IgG The method combines both negative and positive design strategies along with structural and computational modeling guided protein engineering techniques to mutate multiple amino acids of the IgG1CH3 region, and thereby forming a heterodimeric IgG that is stable and has a low homodimer impurity content.

Programmed death receptor-1 (programmed death-1, PD-1) is a recent hot checkpoint (immune checkpoint), belonging to a member of the CD28 family. Unlike other members of the CD28 family, such as CTLA4, which can form divalent bonds to form covalent dimers, PD-1 exists as a monomer. The structure of PD-1 mainly comprises extracellular immunoglobulin variable region-like region, hydrophobic transmembrane region and intracellular region. Its intracellular region contains two independent phosphorylation sites, i.e., the immunoreceptor tyrosine inhibition motif (ITIM) and the immunoreceptor tyrosine transfer motif (ITSM). PD-1 is mainly inducibly expressed on the surface of activated T cells, and also on B cells, NK cells, monocytes, and DC cells. It is mainly involved in the negative regulation of T cell activation and can regulate the strength and duration of immune responses. The ligands of PD-1 include PD-L1 (programmed death ligand 1) and PD-L2 (programmed death ligand 2). Its ligands belong to the B7 family. Among them, PD-L1 is inducibly expressed on the surface of various immune cells including T cells, B cells, monocytes, macrophages, DC cells, and endothelial cells, epidermal cells, etc., while PD-L2 is only inducibly expressed on some immune cells, including macrophages, DC cells, and B cells. In addition to PD-1 ligand, PD-L1 can also be used as a ligand for CD80 to transmit negative regulatory signals to T cells and induce T cell immune tolerance (Autoimmun Rev, 2013, 12(11):1091-1100. Front Immunol, 2013, 4:481. Nat Rev Cancer, 2012, 12(4):252-264. Trends Mol Med. 2015 January; 21(1):24-33. Clin Cancer Res. 2012 Dec. 15; 18(24):6580-7.). Under normal circumstances, PD-1 and PD-L1 can mediate and maintain the autoimmune tolerance of body tissues, prevent the immune system from excessively activating and damaging its own tissues during the inflammatory reaction, and have a positive effect on preventing the occurrence of autoimmune diseases; under pathological conditions, they are involved in the development of tumor immunity and various autoimmune diseases. Many literature reports that PD-L1 is highly expressed in various tumor tissues, PD-1 is highly expressed in tumor-infiltrating lymphocytes, and the overexpression of PD-L1 and PD-1 is closely related to the poor clinical prognosis of tumors. (Anticancer Agents Med Chem. 2015; 15(3):307-13. Hematol Oncol Stem Cell Ther. 2014 March; 7(1):1-17. Trends Mol Med. 2015 January; 21(1):24-33. Immunity. 2013 Jul. 25; 39(1):61-73. J Clin Oncol. 2015 Jun. 10; 33(17):1974-82.). Blocking PD-1/PD-L1, PD-1/PD-L2 with PD-1 monoclonal antibody or blocking PD-1/PD-L1, CD80/PD-L1 with PD-L1 monoclonal antibody have shown good anti-tumor effect both preclinically and clinically. At present, PD-1 monoclonal antibody has been approved by the U.S. FDA for the treatment of various tumors including non-small cell lung cancer, melanoma, head and neck cancer, etc. PD-L1 monoclonal antibody has also been approved for the treatment of non-small cell lung cancer and urothelial cancer. However, only a small proportion of cancer patients can benefit from this type of monoclonal antibody therapy, and most patients do not respond to this type of monoclonal antibody. (Expert Opin Ther Targets. 2014 Dec.; 18(12):1407-20. Oncology (Williston Park). 2014 November; 28 Suppl 3:15-28).

Angiogenesis is a key factor for tumor progression and metastasis, which seriously affects the prognosis of treatment (Nat Rev Drug Discov, 2007, 6:273-286. Cancer Res, 1999, 59:856-861). VEGF signaling pathway mainly includes 6 kinds of ligands (VEGF-A, -B, -C, -D, -E and PGF) and 3 kinds of receptors (VEGFR1, VEGFR2 and VEGFR3). VEGF-A, which is commonly known as VEGF, and its main receptor VEGFR2, are the most important regulatory factors in tumor angiogenesis (Nat Med, 2003, 9:669-676, 2003. J. Biol. Chem., 1991, 266: 11947-11954). As an angiogenic factor, VEGF can increase the permeability of blood vessels, stimulate the proliferation and migration of endothelial cells, promote tumor angiogenesis, and participate in tumor growth, invasion and metastasis. VEGF has been found to have enhanced expression in a variety of human tumors. Its enhanced expression is directly related to the number of angiogenesis in tumor tissues and is closely related to the poor clinical prognosis of tumors. These tumors include breast cancer, colorectal cancer, non-small cell lung cancer, ovarian cancer, etc. (N. Engl. J. Med., 1995, 333: 1757-1763. Gasparini G J. Clin. Oncol., 1995, 13: 765-782.). Blocking the VEGF signaling pathway has shown good anti-tumor effects both preclinically and clinically. At present, VEGF monoclonal antibody has been approved for the treatment of various tumors including non-small cell lung cancer, colorectal cancer, etc. (Int. J. Cancer, 2002, 102: 102-108. Br. J. Cancer, 2001, 85: 584-589. Cancer Res., 2000, 60: 5117-5124. J. Clin. Oncol., 2003; 21: 60-65. J. Clin. Oncol., 2004, 22: 2184-2191.).

Recent studies have found that VEGF is closely related to tumor immunity (Immunity. 2013, 39(1): 61-73. Cancer Metastasis Rev, 2011, 30(1): 83-95.). In the tumor microenvironment, up-regulated expressed VEGF is capable of acting on endothelial cells and inhibit the expression of adhesion molecules, thereby inhibiting the adhesion and infiltration of T cells; VEGF can also up-regulate the expression of various immunosuppressive molecules such as PD-L1, PD-L1, TIM-3, IDO, etc., inhibit the activation of effector T cells. Simultaneously inhibiting PD-1 signal and VEGF signal will have better anti-tumor effect. The animal experimental data and clinical data reported in the literature initially support this strategy (Clin Exp Immunol, 2013, 172(3): 500-6. Sznol et al, ASCO, GU 2015). The combination of PD-1 monoclonal antibody and VEGFR2 monoclonal antibody and the combination of PD-L1 monoclonal antibody and VEGF monoclonal antibody have both shown good synergistic effect.

Combined administration requires sequential injection of two or more antibodies, or the antibody to be made into the same dosage form. However, on the one hand, sequential antibody injections reduce patient compliance and increase pain. On the other hand, due to differences in physicochemical properties of different antibodies, it is difficult or almost impossible to make different antibodies into the same dosage form.

In view of this, it is still necessary to develop a novel therapeutic drug that simultaneously blocks PD-1 and VEGF signaling pathways.

SUMMARY

The present disclosure provides a novel bifunctional antibody that can block PD-1 and VEGF simultaneously with a highly stable heterodimeric form that has natural IgG structural characteristics and free of mismatched heavy and light chain, and preparation method thereof. The bifunctional antibody is more likely to selectively bind to tumor cells that highly express PD-1 and VEGF at the same time, thereby exerting an efficient and specific killing effect while having low toxic and side effects.

A first aspect of the present disclosure relates to a heterodimeric form bispecific antibody comprising a first antigen-binding functional region that is capable of specifically binding to PD-1 and a second antigen-binding functional region that is capable of specifically binding to VEGF, wherein the bispecific antibody comprises a first Fc chain and a second Fc chain with interchain-link through one or more disulfide bonds, the first Fc chain and the second Fc chain are respectively connected to the PD-1 antigen-binding functional region and the VEGF antigen-binding functional region through a covalent bond or a linker, alternatively, the first Fc chain and the second Fc chain are respectively connected to the VEGF antigen-binding functional region and the PD-1 antigen-binding functional region through a covalent bond or a linker; and the first Fc chain and the second Fc chain comprise 5 amino acid substitutions at the following positions:

amino acid substitutions at positions 366 and 399 on the first Fc chain, and amino acid substitutions at positions 351, 407, and 409 on the second Fc chain, the first Fc chain and the second Fc chain comprising the above-mentioned amino acid substitutions are more likely to form a heterodimer with each other instead of a homodimer, wherein amino acid positions are numbered according to the Kabat EU index numbering system.

In some embodiments, amino acid substitutions of the first Fc chain and the second Fc chain are as follows,
a) substitution with glycine, tyrosine, valine, proline, aspartic acid, glutamic acid, lysine or tryptophan at position 351;
b) substitution with leucine, proline, tryptophan or valine at position 366;
c) substitution with cysteine, asparagine, isoleucine, glycine, arginine, threonine or alanine at 399;
d) substitution with leucine, alanine, proline, phenylalanine, threonine or histidine at position 407; and
e) substitution with cysteine, proline, serine, phenylalanine, valine, glutamine or arginine at position 409.

In some embodiments, the amino acid substitutions comprise:
a) substitutions T366L and D399R of the first Fc chain, and substitutions L351E, Y407L and K409V of the second Fc chain;
b) substitutions T366L and D399C of the first Fc chain, and substitutions L351G Y407L and K409C of the second Fc chain;
c) substitutions T366L and D399C of the first Fc chain, and substitutions L351Y, Y407A and K409P of the second Fc chain;
d) substitutions T366P and D399N of the first Fc chain, and substitutions L351V, Y407P and K409S of the second Fc chain;
e) substitutions T366W and D399G of the first Fc chain, and substitutions L351D, Y407P and K409S of the second Fc chain;
f) substitutions T366P and D399I of the first Fc chain, and substitutions L351P, Y407F and K409F of the second Fc chain;
g) substitutions T366V and D399T of the first Fc chain, and substitutions L351K, Y407T and K409Q of the second Fc chain; or
h) substitutions T366L and D399A of the first Fc chain, and substitutions L351W, Y407H and K409R of the second Fc chain.

In some embodiments, the amino acid substitutions of the first Fc chain are T366L and D399R, and the amino acid substitutions of the second Fc chain are L351E, Y407L, and K409V.

In some embodiments, the Fc chain is derived from IgG.

In some embodiments, the PD-1 and VEGF antigen-binding functional regions are selected from a Fab fragment, a scFv fragment, a variable region fragment Fv, and a heavy chain variable region fragment VHH of a heavy chain antibody.

In some embodiments, the PD-1 and VEGF antigen-binding functional regions are Fab fragments or scFv fragments.

In some embodiments, the PD-1 and VEGF antigen-binding functional regions are both Fab fragments.

In some embodiments, one of the PD-1 and VEGF antigen-binding functional regions is a Fab fragment and the other is an scFv.

In some embodiments, the Fab fragment comprises a first heavy chain variable region and a different second heavy chain variable region, and a first light chain variable region and a different second light chain variable region.

In some embodiments, when the first Fc chain and the PD-1 antigen-binding functional region connected thereto, the second Fc chain and the VEGF antigen-binding functional region connected thereto, the first Fc chain and the VEGF antigen-binding functional region connected thereto and the second Fc chain, or the PD-1 antigen-binding functional region connected thereto, present alone and an reducing agent presents at the same time, the weight ratio of formed homodimers is less than 50%.

In some embodiments, the amino acid sequence of the bispecific antibody is selected from SEQ ID NOs: 2, 4, 6, 8, 10, 12, 14, 16, 18, 20, and 22. In some embodiments, the amino acid sequence of the bispecific antibody is the corresponding combination of SEQ ID NO: 2, 4, 6, 8, 10, 12, 14, 16, 18, 20, and 22.

A second aspect of the present disclosure relates to an isolated polynucleotide encoding the heterodimeric form bispecific antibody described in the first aspect.

In some embodiments, the sequence of the polynucleotide is selected from SEQ ID NOs: 1, 3, 5, 7, 9, 11, 13, 15, 17, 19, and 21. In some embodiments, the sequence of the polynucleotide is the corresponding combination of SEQ ID NOs: 1, 3, 5, 7, 9, 11, 13, 15, 17, 19, and 21.

A third aspect of the present disclosure relates to a recombinant expression vector comprising the isolated polynucleotide described in the second aspect.

In some embodiments, the expression vector is a plasmid vector XOGC engineered based on pcDNA.

A fourth aspect of the present disclosure relates to a host cell comprising the isolated polynucleotide described in the second aspect, or the recombinant expression vector described in the third aspect.

In some embodiments, the host cell is selected from human embryonic kidney cell HEK293 or HEK293T, HEK293F, HEK293E engineered based on HEK293 cell; hamster ovary cell CHO, or CHO-S, CHO-dhfr⁻, CHO/DG44, ExpiCHO engineered based on CHO cell; *E. coli*, or *E. coli* BL21, BL21(DE3), Rosetta, Origami engineered based on *E. coli*; a yeast, or *Pichia pastoris, Saccharomyces cerevisiae, Kluyveromyces lactis, Hansenula polymorpha* engineered based on a yeast; an insect cell, or cells High5, SF9 engineered based on an insect cell; a plant cell; a mammary gland cell and a somatic cell of a mammal.

A fifth aspect of the present disclosure relates to a composition comprising the heterodimeric form bispecific antibody described in the first aspect, or the isolated polynucleotide described in the second aspect, or the recombinant expression vector described in the third aspect, or the host cell described in the fourth aspect, and a pharmaceutically acceptable carrier.

A sixth aspect of the present invention relates to a method of producing the heterodimeric form bispecific antibody described in the first aspect comprising the steps of:
1) expressing the isolated polynucleotide described in the second aspect or the recombinant expression vector described in the third aspect in host cells, respectively;
2) reducing the proteins respectively expressed in the host cells; and
3) mixing the reduced protein and then oxidizing the mixture.

In some embodiments, the host cell is selected from human embryonic kidney cell HEK293, or HEK293T, HEK293F, HEK293F engineered based on HEK293 cell; hamster ovary cell CHO, or CHO-S, CHO-dhfr⁻, CHO/DG44, ExpiCHO engineered based on CHO cell; *E. coli*, or *E. coli* BL21, BL21(DE3), Rosetta, Origami engineered based on *E. coli*; a yeast, or *Pichia pastoris, Saccharomyces cerevisiae, Kluyveromyces lactis, Hansenula polymorpha* engineered based on a yeast; an insect cell, or cells High5, SF9 engineered based on an insect cell; a plant cell; a mammary gland cell and a somatic cell of a mammal.

In some embodiments, the reduction step comprises 1) performing a reduction reaction in the presence of a reducing agent selected from: 2-mercaptoethylamine, dithiothreitol, tris(2-carboxyethyl)phosphine or other chemical derivatives; and 2) removing the reduction agent, for example, performing the reduction reaction in the presence of 0.1 mM or higher concentration of dithiothreitol at 4° C. for at least 3 hours.

In some embodiments, the oxidizing step is oxidizing in air, and also includes performing an oxidation reaction in the presence of an oxidizing agent selected from: L-dehydroascorbic acid or its chemical derivatives, for example, performing the oxidation reaction in the presence of 0.5 mM or higher concentration of L-dehydroascorbic acid at 4° C. for at least 5 hours.

In some embodiments, the method further includes a step of separation and purification.

A seventh aspect of the present disclosure relates to use of the heterodimeric form bispecific antibody described in the first aspect and/or the isolated polynucleotide described in the second aspect and/or the recombinant expression vector described in the third aspect and/or the host cell described in the fourth aspect and/or the composition described in the fifth aspect in the preparation of a medicament for preventing and/or treating a disease in a subject.

A eighth aspect of the present disclosure relates to the heterodimeric form bispecific antibody described in the first aspect and/or the isolated polynucleotide described in the second aspect and/or the recombinant expression vector described in the third aspect and/or the host cell described in the fourth aspect and/or the composition described in the fifth aspect, as a medicament for preventing and/or treating a disease in a subject.

A ninth aspect of the present disclosure relates to a method of preventing and/or treating a disease comprising administering the heterodimeric form bispecific antibody described in the first aspect and/or the isolated polynucleotide described in the second aspect and/or the recombinant expression vector described in the third aspect and/or the host cell described in the fourth aspect and/or the composition described in the fifth aspect to a subject in need thereof.

In some embodiments, the subject is a mammal, preferably, a human subject.

In some embodiments, the disease is selected from the following tumors: leukemia, lymphoma, myeloma, brain tumors, squamous cell carcinoma of the head and neck, non-small cell lung cancer, nasopharyngeal cancer, esophageal cancer, gastric cancer, pancreatic cancer, gallbladder cancer, liver cancer, colorectal cancer, breast cancer, ovarian cancer, cervical cancer, endometrial cancer, uterine sarcoma, prostate cancer, bladder cancer, renal cell carcinoma, melanoma.

The present invention designs a brand new anti-PD-1/anti-VEGF natural antibody structure-like heterodimeric form bispecific antibody, it has natural IgG characteristics and free of mismatched heavy and light chains, and is a highly stable, heterodimeric form anti-PD-1/anti-VEGF bispecific antibody. The bispecific antibody is capable of simultaneously binding with two target molecules PD-1 and VEGF, and provides improved efficacy in treating a complex disease. The bispecific antibody prepared by the present disclosure simultaneously blocks the PD-1 signal pathway and the VEGF signal pathway, which is convenient for patients and medical workers to use and simplifies the development process of new drugs.

DETAILED DESCRIPTION

Definition

Figure 1:
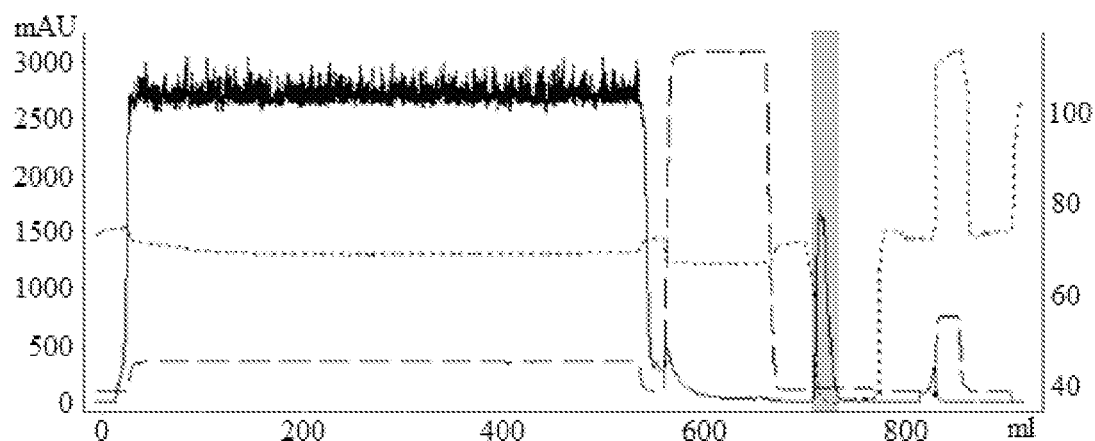
FIG. 1 shows the elution peak chromatogram of anti-PD-1 (Pembro)-Fc1.

Covalent connection refers to that in a heterodimeric form bispecific antibody, two Fc chains, either Fc chain and the antigen-binding functional region connected to it, are connected into a molecule by a covalent bond. Wherein the Fc chain comprises a first antigen-binding functional region and a second antigen-binding functional region connected through one or more covalent connections (such as disulfide bonds); the first Fc chain and the second Fc chain are respectively connected to an antigen-binding functional region by a covalent connection (such as an imine bond or an amide bond).

The antigen-binding functional region refers to a region that can specifically interact with a target molecule such as an antigen, its action is highly selective, and a sequence that recognizes one target molecule usually cannot recognize other molecular sequences. Representative antigen-binding functional region includes: antibody variable regions, structural variants of antibody variable regions, receptor binding regions, ligand binding regions, or enzyme binding regions.

The "interchain-link through a one or more disulfide bonds" refers to that the first Fc chain and the second Fc chain are connected to each other through one or more disulfide bonds to form a heterodimer fragment. In the present disclosure, the formation of one or more disulfide bonds may be formed when the first Fc chain and the second Fc chain or the first Fc chain and the second Fc chain and the antigen-binding functional regions connected thereto are synthesized in the same cell, or may also be formed respectively when the first Fc chain and the second Fc chain or the first Fc chain and the second Fc chain and the antigen-binding functional regions connected thereto are synthesized in different cells, and then formed by a reduction-oxidation method in vitro.

The first Fc chain and the second Fc chain refer to a binding fragment composed of covalent connection. The covalent connection includes disulfide bonds, each chain comprises at least a part of the constant region of the immunoglobulin heavy chain; and the first Fc chain and the second Fc chain are different in amino acid sequence, including at least one amino acid difference. For the first Fc chain and the second Fc chain in the present disclosure, there is a strong mutual repulsion between the same chains, and there is mutual attraction between different chains. Therefore, when the first Fc chain and the second Fc chain, or the first Fc chain and the second Fc chain and the antigen-binding functional regions connected thereto are co-expressed in a cell, they are more likely to form heterodimers. When the first Fc chain and the second Fc chain, or the first Fc chain and the second Fc chain and the antigen-binding functional regions connected thereto, are respectively expressed in two host cells, the first Fc chain or the first Fc chain and the antigen-binding functional region connected thereto are unlikely to form homodimers, and the second Fc chain or the second Fc chain and the antigen-binding functional region connected thereto are unlikely to form homodimers. In the present disclosure, when the first Fc chain and the second Fc chain, or the first Fc chain and the second Fc chain and the antigen-binding functional regions connected thereto, are respectively expressed in two host cells, and in the presence of a reducing agent, the proportion of homodimer is less than 50%, i.e., the proportion of monomers (one Fc chain or one Fc chain and the antigen-binding functional region connected thereto) is greater than 50%.

Immunoglobulin has a symmetrical structure with four polypeptide chains, wherein two of them are the same heavy chains with relatively long and relatively large molecular weights, containing 450 to 550 amino acid residues, and the relative molecular mass is between 55,000 and 70,000 Da; two of them are the same light chain (L chain) with relatively short and relatively small molecular weight, containing about 210 amino acid residues, and the relative molecular mass is about 24,000 Da. The sequence of about 110 amino acids near the N-terminus of different immunoglobulin heavy and light chains varies greatly, and is called the variable region (V region), while the remaining amino acid sequence near the C-terminus is relatively stable, and is called the constant region (C region). In a heavy chain, the variable region accounts for about ¼ of the length of the heavy chain, and the constant region accounts for about ¾ of the length of the heavy chain. For the five known Igs, IgG(γ), IgA(α), IgD(δ), IgM(μ) and IgE(ε), wherein there are three constant regions in the H chain of the first three types of Igs, i.e. composed of CH1, CH2 and CH3. There are one VH region and four constant regions in the H chain of the latter two types, i.e. CH1 to CH4. The constant region is not only the backbone of the immunoglobulin molecule, but also one of the sites that activates the immune response. Although the embodiments of the present disclosure relate to IgG a person skilled in the art knows that, if desired, the class of antibodies of the present disclosure can be switched by known methods. For example, the original IgM antibody of the present disclosure can be switched to an IgG antibody of the present disclosure via class switching. In addition, class switching techniques can be used to switch one IgG subclass to another, such as from IgG1 to IgG2. Therefore, the effector function of the antibody of the present disclosure can be changed to, for example, IgG1, IgG2, IgG3, IgG4, IgD, IgA, IgE or IgM antibodies by isotype switching, for various therapeutic uses. In one embodiment, the antibody of the present disclosure is an IgG1 antibody, such as IgG1, κ.

A part of the constant region of the present disclosure at least includes the region where the first Fc chain interacts with the second Fc chain. For IgG this region is a part of the amino acid located in the CH3 region, which at least includes GLN347, TYR349, THR350, LEU 351, SER 354, ARG 355, ASP 356, GLU 357, LYS 360, SER 364, THR 366, LEU 368, LYS 370, ASN390, LYS392, THR394, PRO395, VAL 397, ASP399, SER400, PHE405, TYR407, LYS409, LYS439.

The first Fc chain and the second Fc chain are respectively connected to an antigen-binding functional region through a covalent bond or a linker, which refers to that the first Fc chain and the second Fc chain are respectively connected through a covalent bond or linker to an antigen-binding fragment of an antibody, or a single-chain antibody that can recognize an antigen, or a variant of other antibody fragments that can recognize an antigen, or a receptor that can recognize a ligand, or a ligand that can recognize a receptor. Wherein the covalent bond refers to a kind of chemical bond. Two or more atoms share their outer electrons to achieve the state of electron saturation under ideal conditions, such that a relatively stable chemical structure is formed, which is called a covalent bond. In other words, a covalent bond is an interaction formed between atoms by sharing electron pairs. Atoms of the same element or different elements can be connected by a covalent bond. For the covalent bond between the first Fc chain and the second Fc chain of the present disclosure, it includes but is not limited to an amide bond formed by dehydration reaction of an amino group of one molecule of amino acid with a carboxyl group of another molecule of amino acid, or an amide bond or imine bond formed by an aldehyde group of ethylene glycol or polyethylene glycol or other compounds or their polymers and an amino group of one molecule of amino acid. Wherein the linker is a segment of amino acid sequence or a compound or a polymer of a compound that can connect two polypeptide chains by a covalent bond. Wherein the segment of the amino acid sequence includes but is not limited to a small peptide, such as GGGGSGGGGSGGGGS, which connects the first Fc chain or the second Fc chain, and a single chain antibody that can recognize an antigen, or other antibody fragment structural variants that can recognize an antigen, through an amide bond.

The first Fc chain and the second Fc chain are more likely to form heterodimers with each other instead of homodimers refers to that since in the first Fc chain and the second Fc chain, there is a mutual repulsion between the same chain and there is mutual attraction between different chains, therefore when the first Fc chain and the second Fc chain, or the first Fc chain and the second Fc chain and the antigen-binding functional regions connected thereto are co-expressed in a cell, they are more likely to form heterodimers. When the first Fc chain and the second Fc chain, or the first Fc chain and the second Fc chain and the antigen-binding functional regions connected thereto, are respectively expressed in two host cells, the first Fc chain or the first Fc chain and the antigen-binding functional region connected thereto are unlikely to form homodimers, and the second Fc chain or the second Fc chain and the antigen-binding functional region connected thereto are unlikely to form homodimers.

The Kabat EU index numbering system refers to that Kabat used a method to assign a number to each amino acid of an antibody sequence and this method of assigning a number to each residue has become a standard method in the art. The Kabat protocol can be extended to other antibodies that are not present in his research, based on conserved amino acids, the target antibody is aligned with one of the consensus sequences identified by Kabat.

The Fc domain refers to the fragment crystallizable (Fc), which is equivalent to the CH2 and CH3 domains of Ig, and is the site where Ig interacts with effector molecules or cells.

IgG is the abbreviation of Immunoglobulin G (IgG), which is the main antibody component of serum. According to the r chain antigenic difference in IgG molecules, human IgG has four subtypes: IgG1, IgG2, IgG3, and IgG4.

The half antibody molecule refers to a structure formed by one heavy chain and one light chain of an antibody, wherein the heavy chain and the light chain may be connected by a covalent bond or not be connected by a covalent bond, and it is a monovalent antibody structure that recognizes an antigen.

The Fab fragment is a kind of molecular recognition sequence, which is the fragment of antigen binding (Fab), and is equivalent to two arms of an antibody molecule, composed of a complete light chain and heavy chain VH and CH1 regions.

The Fv fragment is the smallest functional fragment in an antibody molecule that retains the antigen binding site. It is composed of a light chain variable region and a heavy chain variable region, and the two are bound together by a non-covalent bond.

The scFv fragment is a molecular recognition sequence, and is a structural isomer of an antibody fragment obtained by genetic engineering of the light chain variable region and heavy chain variable region of an antibody. An extracellular region of a membrane receptor is a molecular recognition sequence. The membrane receptors usually include extracellular regions located outside the cell that can recognize and bind to the corresponding antigen or ligand, transmembrane regions that anchor the receptor on the cell surface, and intracellular regions that have kinase activity or can transmit signaling pathways within the cell. A ligand of the cell membrane receptor refers to a protein, small peptide or compound that can be recognized and bound by the extracellular region of the membrane receptor. Cytokines are low-molecular-weight soluble proteins produced by a variety of cells induced by immunogens, mitogens, or other stimulants, and have multiple functions such as regulating innate and adaptive immunity, hematopoiesis, cell growth, APSC pluripotent cells, and damaged tissue repair. Cytokines can be divided into interleukins, interferons, tumor necrosis factor superfamily, colony stimulating factors, chemokines, growth factors, etc. Protein expression tag refers to a segment of an amino acid sequence added at the N-terminus or C-terminus of a target protein, which may be a small peptide or a long amino acid. The addition of the tags can facilitate the correct folding of proteins, can facilitate the separation and purification of proteins, and can facilitate reducing the degradation of proteins in cells. Common tags include but are not limited to HA, SUMO, His, GST, GFP, and Flag.

The VHH fragment is a separate variable region of heavy-chain antibody, which has antigen-binding ability.

The antibody applicable to the heterodimeric form bispecific antibody of the present disclosure is not limited. Preferably, antibodies known in the prior art that can be used to treat and/or prevent diseases can be used in the present disclosure.

The heterodimeric form bispecific antibodies of the present disclosure may have one or more substitutions, deletions, additions and/or insertions. For example, certain amino acids can replace other amino acids in protein structures without significant loses of the ability to bind to other polypeptides (such as antigens) or cells. Since the binding ability and the nature of the protein determine the biological functional activity of the protein, certain amino acid sequence substitutions can be made on the protein sequence without significant loses of their biological utility or activity.

In many cases, polypeptide variants contain one or more conservative substitutions. The "conservative substitution" refers to where amino acids are replaced with other amino acids having similar properties, such that a person skilled in the art of peptide chemistry can expect that the secondary structure and hydrophilic properties of the polypeptide will not substantially change.

Amino acid substitutions are generally based on the relative similarity of amino acid side chain substituents, such as their hydrophobicity, hydrophilicity, charge, size, etc. Exemplary substitutions that take the various aforementioned features into account are well known to a person skilled in the art and include: arginine and lysine; glutamic acid and aspartic acid; serine and threonine; glutamine and asparagine; and valine, leucine and isoleucine.

The term "identity" used in the present disclosure has a generally known meaning in the art, a person skilled in the art is also familiar with rules and standards for determining the identity between different sequences, and it refers to the percentage of polynucleotide or polypeptide sequence variant residues that are the same as the non-variant sequence after sequence alignment and the introduction of gaps (to obtain the maximum percentage homology, if necessary). The present disclosure, in the case of satisfying the identity limitation, also requires that the obtained variant sequence has the biological activity possessed by the parent sequence. a person skilled in the art knows the methods and means regarding how to use the above activities to screen for variant sequences. a person skilled in the art can easily obtain such variant sequences under the teaching of the disclosure of the present application. In specific embodiments, the polynucleotide and polypeptide variants have at least about 70%, at least about 75%, at least about 80%, at least about 90%, at least about 95%, at least about 98%, or at least about 99%, or at least about 99.1%, 99.2%, 99.3%, 99.4%, 99.5%, 99.6%, 99.7%, 99.8%, or 99.9% polynucleotide or polypeptide identity with the polynucleotides or polypeptides described in the present disclosure. Due to the redundancy of the genetic code, there will be variants of these sequences that encode the same amino acid sequence.

In another embodiment of the present disclosure, a polynucleotide composition is provided that it is capable of hybridizing with a polynucleotide sequence or a fragment thereof or a complementary sequence thereof provided by the present disclosure under moderate to high stringency conditions. Hybridization technology is well known in the field of molecular biology. For illustrative purposes, the suitable moderate stringency conditions for testing the hybridization of the polynucleotide of the present disclosure with other polynucleotides include pre-washing in a solution of 5×SSC, 0.5% SDS, 1.0 mM EDTA (pH 8.0); hybridizing under the condition of 50-60° C., 5×SSC, overnight; then respectively washing twice with 2×, 0.5× and 0.2×SSC containing 0.1% SDS for 20 minutes at 65° C. a person skilled in the art understands that the stringency of hybridization can be easily manipulated, for example, by changing the salt content of the hybridization solution and/or the temperature at which hybridization is performed. For example, in another embodiment, suitable high stringency hybridization conditions include those conditions described above, the difference is that the hybridization temperature is increased, for example to reach 60-65° C. or 65-70° C.

The host cell of the present disclosure may be all cells used for foreign gene expression, including but not limited to *E. coli*, yeast, insect cells, plant cells, mammalian cells.

The vector of the present disclosure includes vectors that can replicate in any type of cell or organism, including, for example, plasmids, bacteriophages, cosmids, and mini-chromosomes. In some embodiments, the vector comprising the polynucleotide of the present disclosure is a vector suitable for propagation or replication of the polynucleotide, or a vector suitable for expressing the polypeptide of the present disclosure. Such vectors are known in the field and are commercially available.

The "vector" includes shuttle vectors and expression vectors. Generally, a plasmid construct also includes an origin of replication (such as the ColE1 origin of replication) and a selection marker (such as ampicillin or tetracycline resistance) for plasmid replication and selection in bacteria, respectively. The "expression vector" refers to a vector comprising control sequences or regulatory elements required for expression of the antibody (including antibody fragments) of the present disclosure in bacteria or eukaryotic cells.

The vector of the present disclosure may be all vectors used for the expression of foreign genes, including but not limited to plasmid vectors, wherein the plasmid vectors at least comprise replication initiation sites, promoters, target genes, multiple cloning sites, selection marker genes, preferably, the vectors of the present disclosure include but are not limited to plasmid vectors engineered based on pcDNA, such as X0GC vectors.

The subject of the present disclosure includes poultries, reptiles, mammals, etc. Preferably, the mammals include rodents, primates, and preferably, the primates include humans.

The scope of the diseases involved in the present disclosure includes but is not limited to tumors. Preferably, the tumors include leukemia, lymphoma, myeloma, brain tumor, squamous cell carcinoma of the head and neck, non-small cell lung cancer, nasopharyngeal cancer, esophageal cancer, gastric cancer, pancreatic cancer, gallbladder cancer, liver cancer, colorectal cancer, breast cancer, ovarian cancer, cervical cancer, endometrial cancer, uterine sarcoma, prostate cancer, bladder cancer, renal cell carcinoma, melanoma.

The pharmaceutically acceptable carrier refers to a conventional pharmaceutical carrier in the pharmaceutical field, for example, diluents, excipients, water, etc., fillers such as starch, sucrose, lactose, microcrystalline cellulose, etc.; binders such as cellulose derivatives, alginate, gelatin and polyvinylpyrrolidone; wetting agents such as glycerin; disintegrants such as sodium carboxymethyl starch, hydroxypropyl cellulose, croscarmellose, agar, calcium carbonate and sodium bicarbonate; absorption accelerators such as quaternary ammonium compounds; surfactants such as cetyl alcohol, sodium lauryl sulfate; adsorption carriers such as kaolin and soap clay; lubricants such as talc, calcium and magnesium stearate, micronized silica gel and polyethylene glycol, etc. In addition, other adjuvants such as flavors, sweeteners, etc. may also be added to the composition.

The present disclosure will be further illustrated through the following non-limiting examples. It is well known to a person skilled in the art that a number of modifications may be made to the present disclosure without departing from the principles of the disclosure, and such modifications also fall within the scope of the present disclosure.

Unless otherwise specified, the following experimental methods are conventional methods, and unless otherwise specified, the used experimental materials can be easily obtained from commercial companies. All the antibodies used in the following examples of the present disclosure are standard antibodies derived from commercial sources.

Example 1 Vector Construction of Anti-PD-1/VEGF Heterodimeric Antibody

X0GC expression vectors respectively containing heavy and light chains of anti-human PD-1 antibody PD-1 (Pembro) were constructed. The nucleotide sequence of the light chain variable region is shown in SEQ ID NO: 9, the amino acid sequence is shown in SEQ ID NO: 10; the nucleotide sequence of the light chain constant region is shown in SEQ ID NO: 3, and the amino acid sequence is shown in SEQ ID NO: 4; the nucleotide sequence of the heavy chain variable region is shown in SEQ ID NO: 11, and the amino acid sequence is shown in SEQ ID NO: 12; the nucleotide sequence of the heavy chain constant region is shown in SEQ ID NO: 13, and the amino acid sequence is shown in SEQ ID NO: 14, and this heavy chain sequence was named PD-1(Pembro)-Fc1. The light chain variable region and the light chain constant region, the heavy chain variable region and the heavy chain constant region are respectively amplified by PCR. All PCR reactions in this application used Phusion Ultra-Fidelity DNA Polymerase (F-530L) from NEB. PCR primers were conventionally designed according to the principle of base complementarity and the need for restriction sites. The reaction systems were all: 8.9 µl of $H_2O$, 4 µl of 5× Phusion ultra-fidelity DNA polymerase buffer, 4 µl of 1 mM dNTP, 1 µl of upstream primer, 1 µl of downstream primer, 0.1 µl of Phusion ultra-fidelity DNA polymerase, 1 µl of template. The PCR products of the variable regions and the constant regions were subjected to 1.5% agarose gel electrophoresis, and the corresponding fragments were recovered with a DNA recovery kit (Promega, A9282, the same below). The recovered variable region fragments and constant region fragments were used as templates, the upstream primers of the variable regions and the downstream primers of the constant regions were used to perform another round of PCR reaction. Then the corresponding fragments were recovered to obtain full-length fragments of the heavy chain and the light chain. The X0GC vectors and full-length fragments were digested with EcoRI (NEB, Catalog No. R3101L) and HindIII (NEB, Catalog No. R3104L). The digestion reaction system was: 32 µl of 10× buffer, 0.5 µl of EcoRI and HindIII, respectively, 3 µl of the full-length fragment obtained by gel recovery, 14.5 µl of $H_2O$. The digestion system was reacted at 37° C. for 3 hours. The digested products were connected with T4DNA ligase (NEB, Catalog No. M0202V) (the same below), and the reaction system was: 2 µl of 10× ligase buffer, 0.5 µl of ligase, 3 µl of full-length fragment obtained by gel recovery, 3 µl of X0GC vector obtained by gel recovery, 11.5 µl of $H_2O$. The connection was performed by reaction at room temperature for 12 hours. The ligation products were transformed into *E. coli* competent cell DH5α (Tiangen, CB104, the same below). The X0GC expression vectors of antibody heavy and light chains were obtained and used to express the heavy and light chains of antibodies in eukaryotic cells, respectively.

At the same time, the present disclosure respectively constructed X0GC expression vectors of heavy chain and light chain of another anti-human PD-1 antibody PD-1 (BJHM). Wherein the nucleotide sequence of the light chain variable region is shown in SEQ ID NO: 15, the amino acid sequence is shown in SEQ ID NO: 16; the nucleotide sequence of the light chain constant region is shown in SEQ ID NO: 3, the amino acid sequence is shown in SEQ ID NO: 4; the nucleotide sequence of the heavy chain variable region is shown in SEQ ID NO: 17, the amino acid sequence is shown in SEQ ID NO: 18; the nucleotide sequence of the heavy chain constant region is shown in SEQ ID NO: 13, and the amino acid sequence is shown in SEQ ID NO: 14, and this heavy chain sequence was named PD-1(BJHM)-Fc1. The heavy chain variable region sequence of the anti-human PD-1 antibody PD-1(BJHM) was connected to another heavy chain constant region sequence, the nucleotide sequence of the heavy chain constant region is shown in SEQ ID NO: 19, the amino acid sequence is shown in SEQ ID NO: 20, and this heavy chain sequence was named PD-1 (BJHM)-Fc2. The X0GC expression vectors of antibody heavy chain and light chain were obtained and used to express the heavy and light chains of antibodies in eukaryotic cells, respectively.

X0GC expression vectors of heavy and light chains of anti-human VEGF antibody VEGF (Bevaci) were respectively constructed. The nucleotide sequence of the light chain variable region is shown in SEQ ID NO: 1, and the amino acid sequence is shown in SEQ ID NO: 2; the nucleotide sequence of the light chain constant region is shown in SEQ ID NO: 3, and the amino acid sequence is shown in SEQ ID NO: 4; the nucleotide sequence of the heavy chain variable region is shown in SEQ ID NO: 5, and the amino acid sequence is shown in SEQ ID NO: 6; the nucleotide sequence of the heavy chain constant region is shown in SEQ ID NO: 13 and the amino acid sequence is shown in SEQ ID NO: 14, and this heavy chain sequence was named VEGF(Bevaci)-Fc1. The heavy chain variable region sequence of the anti-human VEGF antibody VEGF (Bevaci) was connected to another heavy chain constant region sequence, the nucleotide sequence of the heavy chain constant region is shown in SEQ ID NO: 19, and the amino acid sequence is shown in SEQ ID NO: 20, and this heavy chain sequence was named VEGF(Bevaci)-Fc2. The X0GC expression vectors of antibody heavy chain and light chain were obtained and used to express the heavy and light chains of antibodies in eukaryotic cells, respectively.

At the same time, the present disclosure respectively constructed X0GC expression vectors of heavy chain and light chain of another anti-human VEGF antibody VEGF (G631). Wherein the antibody variable region sequence was derived from US20060280747. The nucleotide sequence of the light chain variable region is shown in SEQ ID NO: 7, the amino acid sequence is shown in SEQ ID NO: 8; the nucleotide sequence of the light chain constant region is shown in SEQ ID NO: 3, and the amino acid sequence is shown in SEQ ID NO: 4; the nucleotide sequence of the heavy chain variable region is shown in SEQ ID NO: 21, and the amino acid sequence is shown in SEQ ID NO: 22; the nucleotide sequence of the heavy chain constant region is shown in SEQ ID NO: 19, and the amino acid sequence is shown in SEQ ID NO: 20, and this heavy chain sequence was named VEGF(G631)-Fc2. The X0GC expression vectors of antibody heavy chain and light chain were obtained and used to express the heavy and light chains of antibodies in eukaryotic cells, respectively.

Example 2 Expression of Anti-PD-1/VEGF Heterodimeric Antibody

The expression vectors containing the heavy and light chains of anti-human PD-1 antibody were transfected into 293F cells (FreeStyle™ 293-F Cells, Catalog No. R79007, invitrogen), respectively. Besides, the expression vectors containing the heavy and light chains of anti-human VEGF antibody were also transfected into 293F cells. The cells were inoculated one day before transfection. The cells were centrifuged and collected on the day of transfection. The cells were resuspended in fresh FreeStyle™ 293 expression medium (FreeStyle™ 293 Expression Medium, Catalog No. 12338001, Gibco) at a cell density of $200 \times 10^5$ cells/mL. Plasmids were added according to the transfection volume, the final concentration was 36.67 ug/mL, and it was mixed gently; then linear PEI (polyethyleneimine, linear, M.W. 25000, Catalog No. 43896, Alfa Aesar) was added, the final concentration was 55 ug/mL, and it was mixed gently. Then it was put into an incubator, and incubated in a shaking incubator at 120 rpm for 1 hour at 37° C. Nineteen transfection volume of fresh medium was added. Incubation in a shaking incubator at 120 rpm at 37° C. was continued. The cell culture supernatant transfected for 5 to 6 days was collected by centrifugation.

The expression amount was measured by ELISA. Precipitates were removed by filtering with a 0.2 μm filter before purification using a chromatography column. This step was performed at 4° C.

Example 3 Purification of Expression Products of Anti-PD-1/VEGF Heterodimeric Antibody AKTA explorer 100 protein purification system (GE Healthcare) and affinity chromatography column rProtein A Sepharose Fast Flow (16 mm I.D., 22 ml, GE Healthcare) were used for purification at 4° C. First, the chromatographic column was equilibrated with mobile phase A (20 mM sodium phosphate buffer, 150 mM sodium chloride, pH 7.4). After the baseline was stable, the cell supernatant after the above treatment was loaded at a flow rate of 5 ml/min, and equilibrated with mobile phase A after loading. The samples were the anti-PD-1 expression product and the anti-VEGF expression product expressed in Example 2, respectively. After that, first, 5 column volumes were washed with mobile phase B1 (mobile phase A containing 0.5 M arginine); then 5 column volume were eluted with mobile phase B2 (100 mM citric acid, pH 3.0), the elution peak was collected as the target protein peak; the flow rates of the above elution steps were all 5 ml/min. The elution peak chromatogram of anti-PD-1 (BJHM)-Fc1 is shown in FIG. 1. The elution peaks of anti-PD-1(Pembro)-Fc1, PD-1(BJHM)-Fc2, VEGF (G631)-Fc2, VEGF(Bevaci)-Fc1, VEGF(Bevaci)-Fc2 were similar (the results are not included). The marked elution peak (the grey area as shown) was collected, the pH was adjusted to 5.0 by dropwise addition of 1M sodium acetate solution.

Example 4 Purification of Anti-PD-1/VEGF Heterodimeric Antibody

Figure 2:
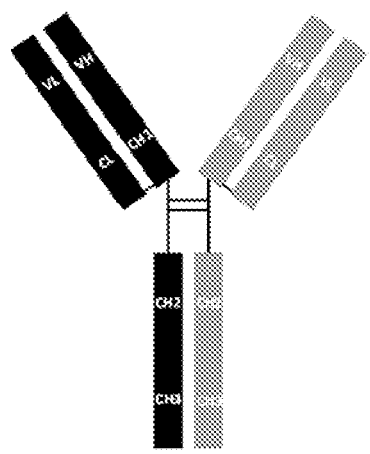
FIG. 2 shows the structure of the anti-PD-1/VEGF heterodimeric antibody molecule.

The structure of the anti-PD-1/anti-VEGF heterodimeric antibody molecule is shown in FIG. 2.

Figure 3:
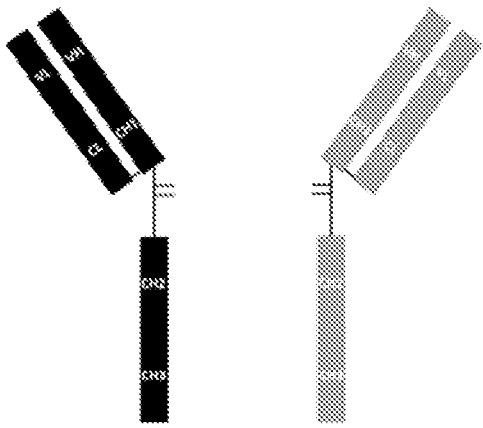
FIG. 3 shows the structure of half-antibody molecules containing one heavy chain and one light chain.
Figure 4:
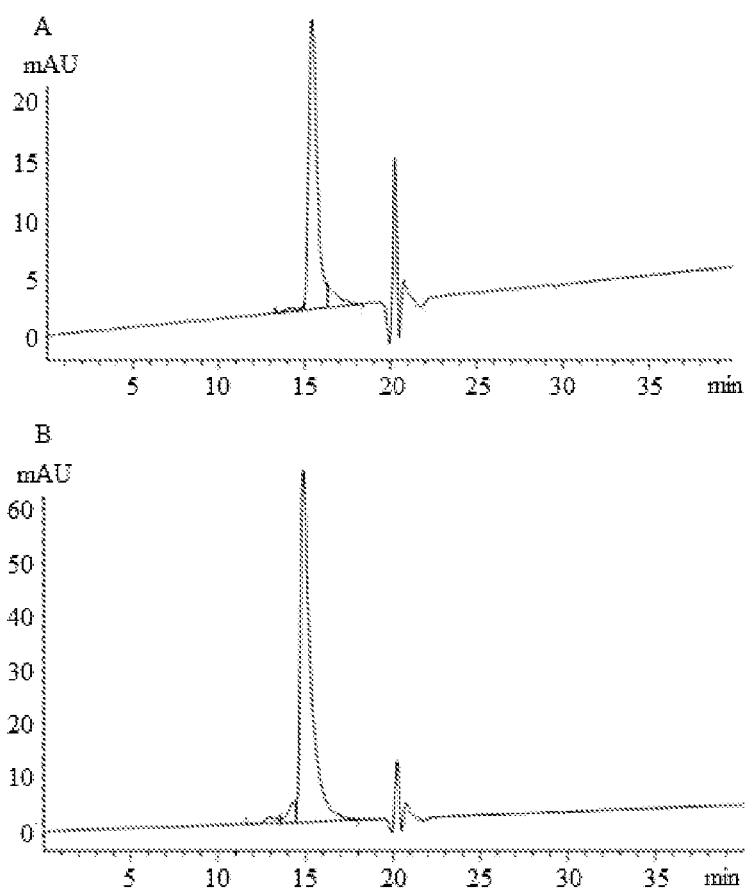
FIG. 4 shows the SEC analysis result of a half-antibody molecule containing one heavy chain and one light chain, wherein Figure A and Figure B respectively represent the PD-1 (Pembro)-Fc1 half antibody molecule and the VEGF (Bevaci)-Fc2 half antibody molecule.

The anti-PD-1 and anti-VEGF expression products obtained by the rProtein A Sepharose Fast Flow (16 mm I.D., 22 ml, GE Healthcare) method in Example 3 above were subjected to in vitro recombination to obtain heterodimers. First, the purified and collected protein solution was concentrated by ultrafiltration through an ultrafiltration concentration tube (nominal cut-off molecular weight 10 kDa), and the solution was replaced with phosphate buffer saline (PBS) PBS (pH=7.4). The obtained anti-PD-1 and anti- VEGF expression products were adjusted to 1 mg/ml with the PBS, respectively, and 1/200 times the final volume of 1M DTT was added, the final concentration of DTT was 5 mM, respectively, and the reduction was carried out at 4° C. (3-8 hours), through the reduction process, the disulfide bond was opened, the disulfide bonds in the hinge region of some of the antibody homodimeric molecules contained in the anti-PD-1 and anti-VEGF expression products were also opened, forming half-antibody molecules containing one heavy chain and one light chain. The structure is shown in FIG. 3. The reduced sample was analyzed by SEC-HPLC with 1 mM DTT reducing agent in the mobile phase buffer, the results are shown in FIGS. 4, A and B. Taking anti-PD-1(BJHM)-Fc1 and anti-VEGF(Bevaci)-Fc2 as examples, the weight ratios of homodimeric molecules were less than 10%, and correspondingly, the weight ratios of half-antibody molecules were both greater than 90%.

Figure 5:
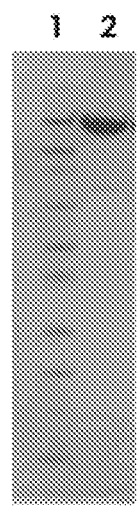
FIG. 5 shows the SDS-PAGE analysis results of oxidation products of the PD-1 (Pembro)-Fc1 half antibody molecule and the VEGF (Bevaci)-Fc2 half antibody molecule.

Then, the reduced anti-PD-1(BJHM)-Fc1 and anti-VEGF (Bevaci)-Fc2 half-antibody molecules were mixed in an equal molar ratio, and the recombination reaction was carried out at 4° C. for 24 hours. In the process of recombination, anti-PD-1(BJHM)-Fc1 and anti-VEGF(Bevaci)-Fc2 half-antibody molecules formed a heterodimeric form bispecific antibody containing anti-PD-1 and anti-VEGF half antibody molecules at the same time through the non-covalent force of CH2/CH3. Then the protein solution was concentrated by ultrafiltration through an ultrafiltration concentration tube (nominal cut-off molecular weight 10 kDa), the solution was replaced with a phosphate solution (PBS, pH=7.4) and the reduction was terminated, and the oxidation reaction was carried out by air or an oxidizing agent, such that the disulfide bond of the heterodimeric form bispecific antibody was reformed. The conditions of the oxidation reaction were adding 100 mM L-dehydroascorbic acid as an oxidizing agent, the final protein concentration was 1 mg/ml, and the final concentration of the oxidizing agent was 1 mM, the oxidation was performed at 4° C., and the reaction was carried out for 24 hours. The samples obtained from the above oxidation reaction were analyzed by SDS-PAGE, and the results were shown in FIG. 5.

Figure 6:
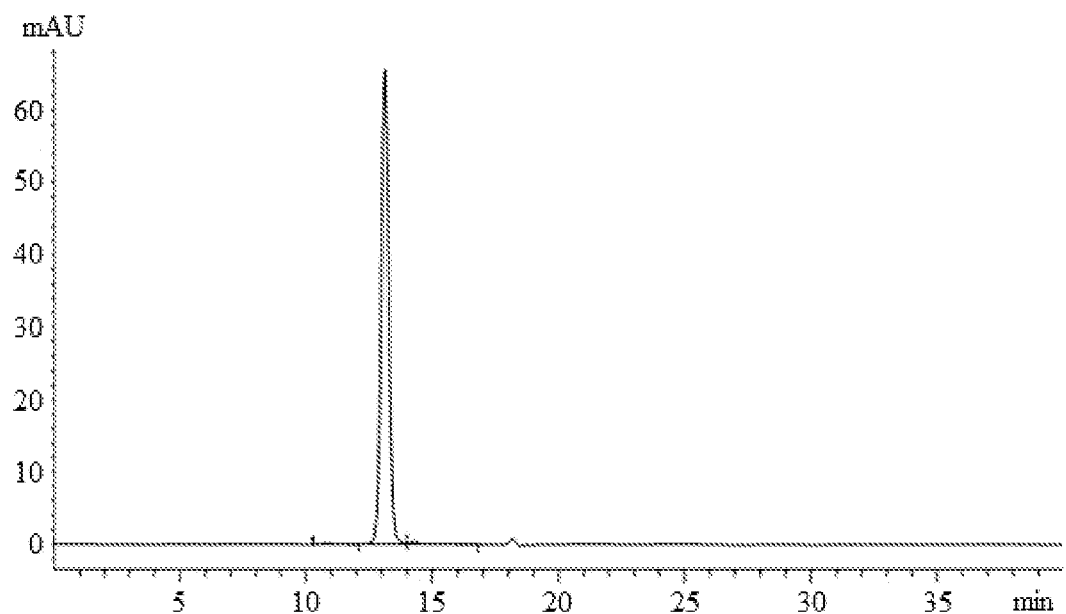
FIG. 6 shows the SEC-HPLC analysis result of the anti-PD-1/VEGF heterodimeric antibody molecule.
Figure 7:
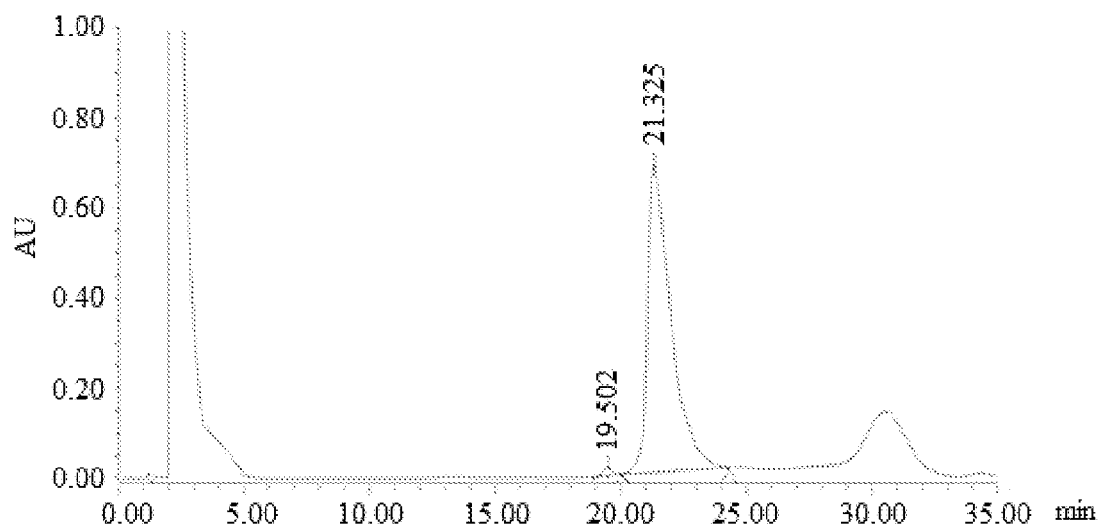
FIG. 7 shows the RPC-HPLC analysis result of the anti-PD-1/VEGF heterodimeric antibody molecule.

The above-mentioned heterodimeric molecules obtained by reduction and oxidation of the anti-PD-1(BJHM)-Fc1 and anti-VEGF(Bevaci)-Fc2 half-antibody molecules were concentrated by ultrafiltration through an ultrafiltration concentration tube (nominal cut-off molecular weight 10 kDa), and the solution was replaced with 10 mM sodium phosphate buffer, pH 5.8. AKTA explorer 100 protein purification system (GE Healthcare) and ion chromatographic column Source 15S (16 mm I.D., 17 ml, GE Healthcare) were used for purification at 4° C. First, the chromatographic column was equilibrated with mobile phase A (10 mM sodium phosphate, pH 7.0). After the baseline was stable, the protein solution after the above treatment was loaded at a flow rate of 3 ml/min, and equilibrated with mobile phase A after loading. Then 20 column volumes were washed (0% B-100% B, 170 min, flow rate 2 ml/min) with a gradient from A (10 mM sodium phosphate, pH 5.8) to B (10 mM sodium phosphate, pH 5.8), the marked elution main peak was collected. The collected protein solution was concentrated by ultrafiltration through an ultrafiltration concentration tube (nominal cut-off molecular weight 10 kDa), and the solution was replaced with a phosphate solution (PBS, pH=7.4), filtered and sterilized and stored at 4° C. The purified product was analyzed for purity by SEC-HPLC, and the result is shown in FIG. 6, and the purity was 98.6%. After RPC-HPLC purity analysis, the result is shown in FIG. 7, and the purity was 98.8%.

Example 5 Target Binding Activity of Anti-PD-1/VEGF Heterodimeric Antibody

Enzyme-linked immunosorbent assay (ELISA) was used to determine the binding ability of the anti-PD-1/VEGF heterodimeric antibodies to a single antigen.

The specific implementation process of ELISA was as follows: Recombinant human PD-1 (Beijing Sino Biological Inc., Catalog No. 10377-H08H) or human VEGF (Beijing Sino Biological Inc., Catalog No. 11066-HNAH) or mouse VEGF (Beijing Sino Biological Inc., Catalog No. 50159-MNAB) was coated on a 96-well high-adsorption ELISA plate with a carbonate buffer solution of pH=9.6, the coating concentration was 1 µg/mL, 100 µL per well. The coating was carried out at 4° C. overnight, washed 5 times with PBST, blocked with PBST containing 5% skim milk and 1% BSA at 300 µL/well, and incubated at 25° C. for one hour, washed 5 times with PBST. Samples of heterodimeric antibodies serially diluted in PBST containing 1% BSA and controls were added, 100 µL was added to each well, and incubated at 25° C. for 1 hour, washed 5 times with PB ST. Then, horseradish peroxidase-labeled anti-human IgG antibody (Chemicon, Catalog No. AP309P) diluted 1:10000 in PBST containing 1% BSA was added, 100 µL was added to each well, and incubated at 25° C. for 1 hour. Washed 5 times with PBST. Colorimetric substrate TMB was added, 100 µL/well, color was developed at room temperature for 10 minutes. 1M $H_2SO_4$ was added, 100 µL/well, the color development was terminated. The absorbance at 450 nm was read on the microplate reader.

Figure 8:
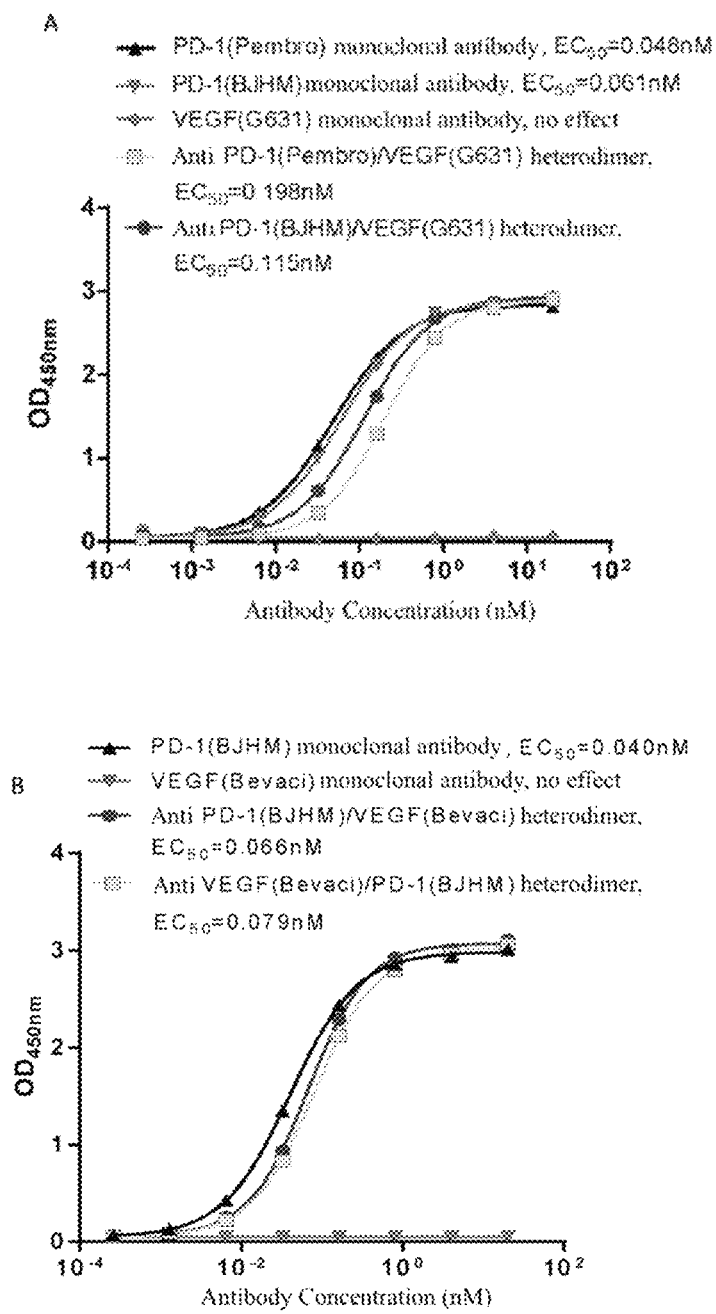
FIG. 8 shows the PD-1 binding activity and VEGF binding activity of the anti-PD-1/VEGF heterodimeric antibody molecule. Among them, Figure A and Figure B show the human PD-1 binding activity, Figure C and Figure D show the human VEGF binding activity, and E shows the mouse VEGF binding activity.
Figure 8:
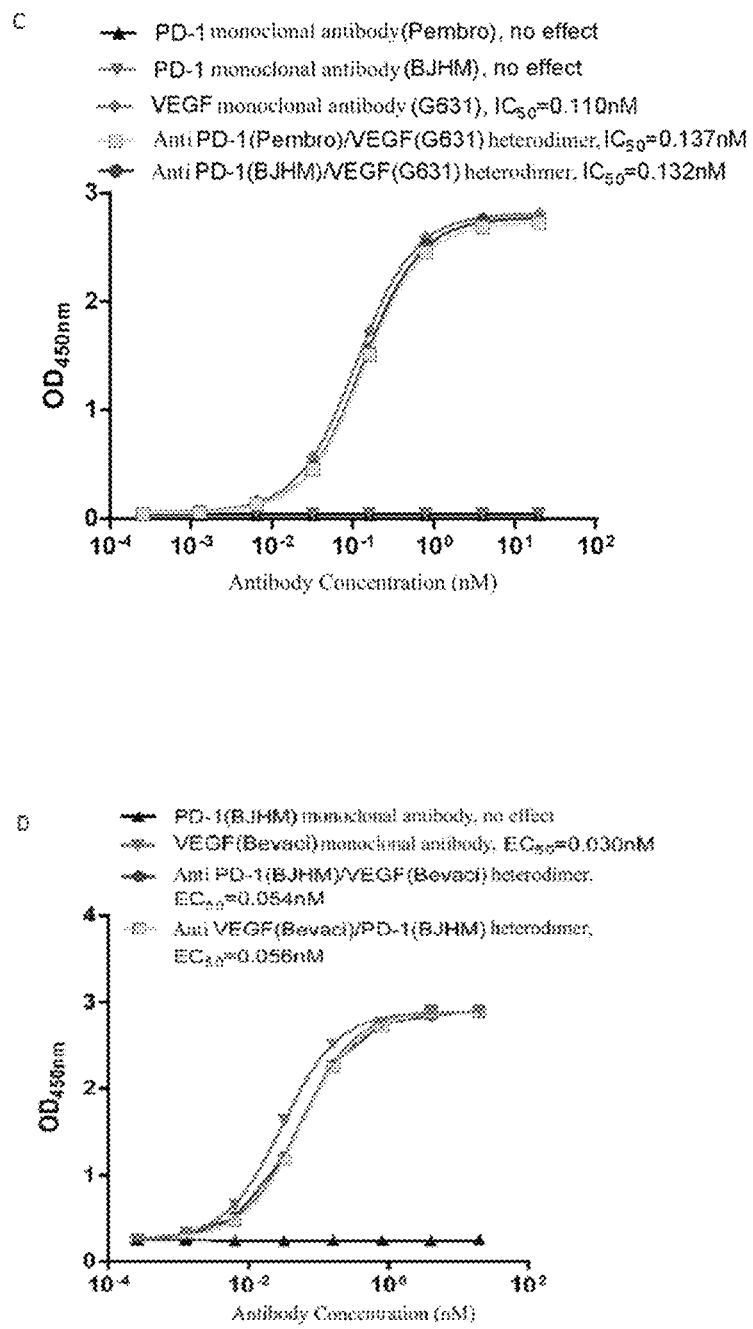

The results are shown in FIGS. 8A and B. The anti-PD-1 (Pembro)/VEGF (G631) heterodimeric antibody, the anti-PD-1 (BJHM)/VEGF (G631) heterodimeric antibody, the anti PD-1(BJHM)/VEGF(Bevaci) heterodimeric antibody and the anti-VEGF(Bevaci)/PD-1(BJHM) heterodimeric antibody all had high affinity to human PD-1; the antigen binding activity was comparable or slightly weaker compared with that of the PD-1 (Pembro) monoclonal antibody and the PD-1 (BJHM) monoclonal antibody. Among them, the heterodimer based on PD-1 (BJHM) had a slightly stronger affinity than the heterodimer based on PD-1 (Pembro). As shown in C and D of FIG. 8, all anti-PD-1/VEGF heterodimer antibodies had high affinity to human VEGF, which was comparable to that of the VEGF (G631) monoclonal antibody and the VEGF (Bevaci) monoclonal antibody. As shown in E of FIG. 8, the anti-PD-1 (Pembro)/VEGF (G631) heterodimer antibody has a high affinity to mouse VEGF, which was comparable to the antigen binding activity of the VEGF (G631) monoclonal antibody.

Example 6 Dual Target Simultaneous Binding Activity of Anti-PD-1/VEGF Heterodimeric Antibody Enzyme-linked immunosorbent assay (ELISA) was used to determine the simultaneous binding ability of the anti-PD-1/VEGF heterodimer antibodies to two different antigens.

The specific implementation process of ELISA was as follows: Recombinant human VEGF (Beijing Sino Biological Inc., Catalog No. 11066-HNAH) was coated on a 96-well high-adsorption ELISA plate with carbonate buffer solution of pH=9.6, the coating concentration was 1 µg/mL, 100 µL per well. The coating was carried out at 4° C. overnight. Washed 5 times with PBST, blocked with PBST containing 1% BSA at 300 µL/well, and incubated at 25° C. for 1 hour, washed 5 times with PBST. Samples of heterodimeric antibodies serially diluted in PBST containing 1% BSA and controls were added, 100 μL was added to each well, and incubated at 25° C. for 1 hour, washed 5 times with PBST. Then, biotin-labeled PD-1-Fc (Beijing Hanmi Pharmaceutical co., Ltd.) diluted in PBST containing 1% BSA was added, 0.5 μg/mL, 100 μL per well, and incubated at 25° C. for 1 hour. Streptavidin-horseradish peroxidase conjugate (BD Pharmingen, Catalog No. 554066) diluted 1:1000 in PBST containing 1% BSA was added, 100 μL was added to each well, and incubated at 25° C. for 1 hour. Washed 5 times with PBST. Colorimetric substrate TMB was added, 100 μL/well, color was developed at room temperature for 10 minutes. 1 M $H_2SO_4$ was added, 100 μL/well, the color development was terminated. The absorbance at 450 nm was read on the microplate reader.

Figure 9:
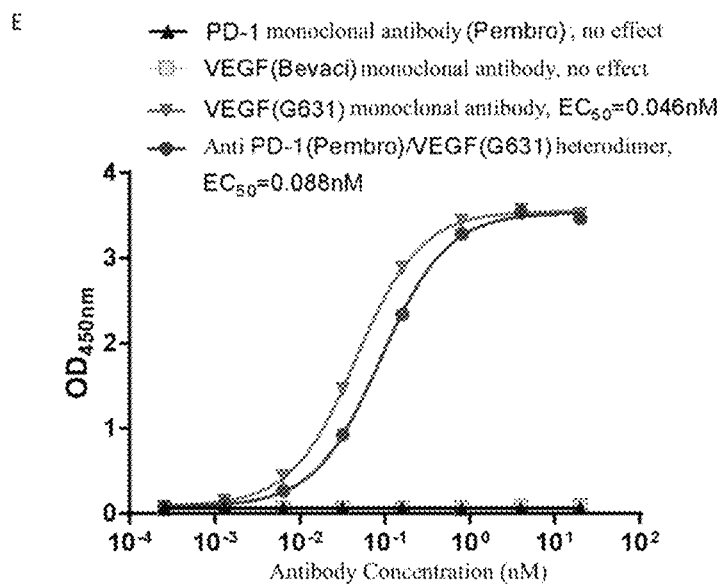
FIG. 9 shows the PD-1 and VEGF simultaneous binding activity of the anti-PD-1/VEGF heterodimeric antibody molecule.
Figure 9:
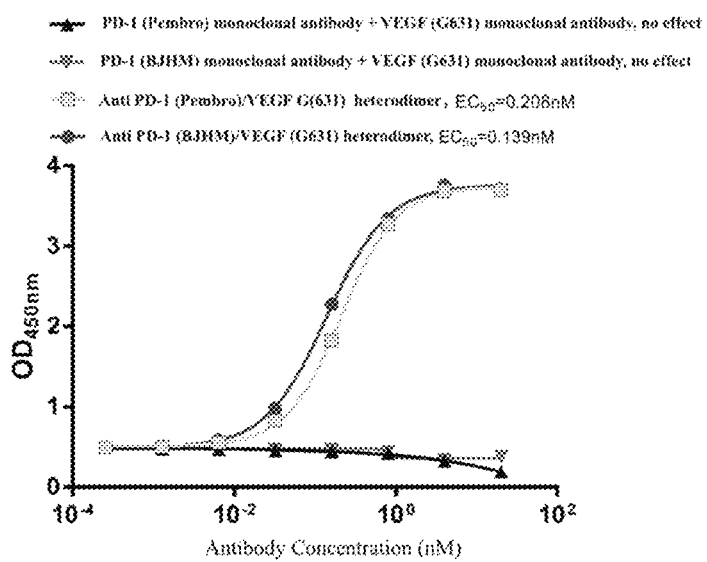

The results are shown in FIG. 9. The combination of PD-1 monoclonal antibody and VEGF monoclonal antibody could not bind to PD-1 and VEGF at the same time, and only the anti-PD-1/VEGF heterodimeric antibody had the activity of binding to two antigens at the same time.

Example 7 VEGF Neutralizing Activity of Anti-PD-1/VEGF Heterodimeric Antibody

The proliferation of human umbilical vein endothelial cells (HUVEC) is regulated by VEGF. The primary cell was used to measure the VEGF neutralizing activity of the anti-PD-1/VEGF heterodimeric antibodies.

Human umbilical vein endothelial cells (HUVEC) were obtained from PromoCell (Catalog No: C-12203). HUVEC cells were cultured in a cell incubator with ECGM-2 medium (PromoCell, Catalog No. C-22011), 37° C., 5% $CO_2$. The analysis medium was ECBM-2 (PromoCell, Catalog No: C-22211) medium containing 0.4% FBS (Hyclone, Catalog No: SH30084.03). The HUVEC were collected by trypsin digestion, washed twice with ECBM-2 medium, resuspended in the analysis medium, the cell density was 1×10E5/mL, and was inoculated at 100 μL/well on a 96-well cell culture plate, i.e. 10,000 cells per well. 50 μL/well of samples of heterodimeric antibodies serially diluted with analysis medium and controls were added, then 50 μL/well of human VEGF (Beijing Sino Biological Inc., Catalog No. 11066-HNAH) diluted with analysis medium was added, and the final concentration was 50 ng/mL. The culture plate was placed in a 37° C., 5% $CO_2$ incubator and incubated for 3 days. At the end of the incubation, 40 μL of MTS (CellTiter96 Aqueous One Solution, Promega, Catalog No: G358B) was added to each well of the cell culture plate to detect cell viability. The cell culture plate was incubated in the incubator for 3-4 hours, and then the absorbance at 490 nm on the microplate reader was read.

Figure 10:
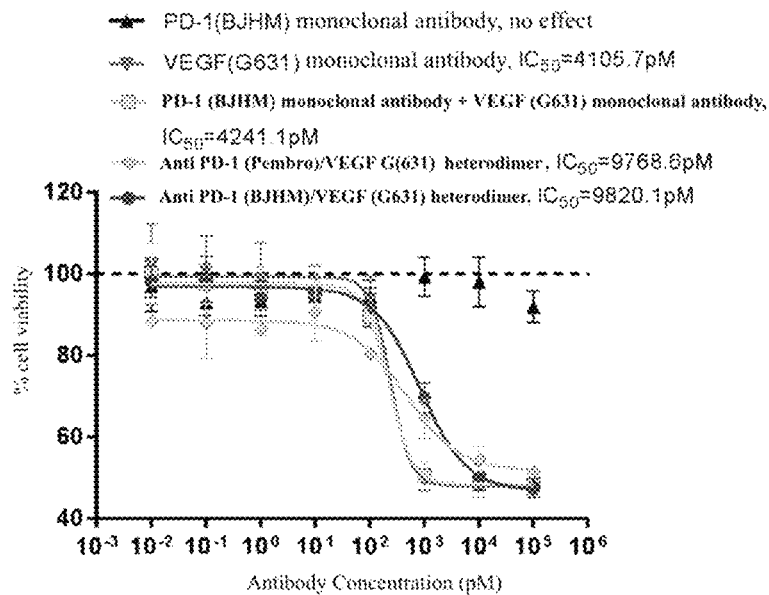
FIG. 10 shows the VEGF neutralizing activity of the anti-PD-1/VEGF heterodimeric antibody molecule.

As shown in FIG. 10, the anti-PD-1/VEGF heterodimeric antibody had good VEGF neutralizing activity, which was comparable to the VEGF monoclonal antibody.

Example 8 T Cell Regulatory Activity of Anti-PD-1/VEGF Heterodimer Antibody

The mixed lymphocyte reaction (MLR) was used to measure the regulatory activity of the anti-PD-1/VEGF heterodimeric antibodies on T cell immune response.

Obtaining human dendritic cells (DC): Human PBMC cells (Lonza, Catalog No. CC-2702) were recovered and collected. Human PBMC cells were resuspended in serum-free RPMI 1640 medium (Gibco, Catalog No: 22400-089) at a cell density of 5×10$^6$/mL and inoculated in cell culture flasks (Nunc, Catalog No: 156367), and was incubated in a carbon dioxide incubator at 37° C. for 90 minutes. The culture supernatant and suspension cells were discarded, and the adherent cells were cultured in complete medium (RPMI 1640 containing 10% FBS), and 100 ng/mL GM-CSF (Beijing Sino Biological Inc., Catalog No. 10015-HNAH) and 100 ng/mL IL-4 (Beijing Sino Biological Inc., Catalog No. 11846-HNAE) were added. Incubation was performed for 3 days, the medium was replaced, and incubated for another 3 days. Then the medium was replaced with a complete medium (RPMI 1640 containing 10% FBS) containing 100 ng/mL GM-CSF, 100 ng/mL IL-4 and 20 ng/mL TNF-α, and incubated for 1 day. DC cells were obtained.

Obtaining human T cells: Human PBMC cells were recovered and collected. It was ensured that this PBMC and the PBMC inducing the DC cells were from different individuals. Human T cells were isolated according to the instruction of the Pan T cell isolation kit (Miltenyi Biotech, Catalog No. 5150414820). Briefly, first the PBMC was washed with PBS (Gibco, Catalog No: 14190-136), then the PBMC was resuspended at $10^7$ cells per 40 μL of separation buffer (PBS containing 2 mM EDTA, 0.5% BSA, pH=7.2) (the following usage amounts are all based on $10^7$ cells), and 10 μL of Pan T cell Biotin Antibody Cocktail was added and incubated at 4° C. for 5 minutes. Then 30 μL of separation buffer and 20 μL of Pan T cell MicroBead Cocktail were added, and incubated at 4° C. for 10 minutes, passed through the MACS separation column (Miltenyi, Catalog No: 130-042-401). T cells were obtained.

The collected human DC cells and human T cells were resuspended in complete medium (RPMI 1640 containing 10% FBS) and inoculated on a 96-well plate. The inoculated DC cells and T cells were 1×10$^4$/well and 1×10$^5$/well, respectively, mixed and cultured. Samples of the heterodimeric antibodies serially diluted with complete medium and controls were added. The culture plate was placed in a 37° C. carbon dioxide incubator and incubated for 5 days. After the incubation, the supernatant in the well was taken out, the cytokine IFN-γ (RayBiotech, Catalog No. ELH-IFNg) was detected according to the kit manual.

Figure 11:
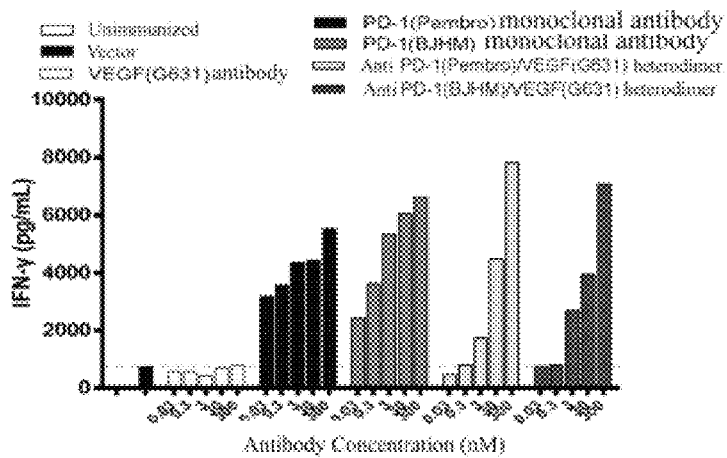
FIG. 11 shows the immunomodulatory activity of the anti-PD-1/VEGF heterodimeric antibody molecule promoting cytokine secretion.

As shown in FIG. 11, human T cells were activated and secreted IFN-γ under the stimulation of allogeneic DC cells. Addition of the PD-1 monoclonal antibody would enhance the activation of T cells and promote the secretion of cytokines, while the VEGF monoclonal antibody did not have this activity. The anti-PD-1/VEGF heterodimer antibodies also showed strong T cell regulatory activity and significantly promoted the secretion of cytokine IFN-γ.

Example 9 Pharmacokinetic Study of Anti-PD-1/VEGF Heterodimeric Antibody in Mice Female BALB/c mice, 6-8 weeks old, were selected as experimental materials, and were purchased from Beijing Huafukang Biotechnology Co., Ltd. After one week of acclimatization to the environment, the mice were randomly divided into groups, 15 mice per group. Each group was administered with the PD-1 (Pembro) monoclonal antibody, the VEGF (G631) monoclonal antibody, and an anti-PD-1 (Pembro)/VEGF (G631) heterodimeric antibody, the doses were all 20 nmol/kg, intraperitoneal injection, single administration. At zero, 1 hour, 3 hours, 6 hours, 10 hours, 24 hours, 48 hours, 72 hours, 96 hours, 120 hours, 168 hours, 216 hours, 264 hours, 336 hours, 408 hours after administration, about 0.2 mL of blood was collected from the orbit, without anticoagulation, the blood sample was placed at room temperature for 30 minutes to 1 hour, after clotting, centrifuged at 3000 rpm for 10 minutes. The obtained serum samples were frozen and stored at −80° C. for testing.

The concentration of the PD-1 (Pembro) monoclonal antibody, the VEGF (G631) monoclonal antibody, and the anti-PD-1 (Pembro)/VEGF (G631) heterodimeric antibody in serum was measured by ELISA. Briefly, the recombinant human PD-1 protein (Beijing Sino Biological Inc., Catalog No. 10377-H08H) or human VEGF (Beijing Sino Biological Inc., Catalog No. 11066-HNAH) was coated on a high-adsorption ELISA plate with a carbonate buffer solution of pH=9.6 at 4° C. overnight. Washed with PBST. In order to prevent non-specific binding, the plate was blocked with PBST containing 5% skimmed milk powder, and washed with PBST. Then, the test serum sample diluted with PBST containing 10% mixed mouse serum and 1% BSA was added and incubated, at 25° C. for 1 hour, and the plate was washed with PBST. Horseradish peroxidase-labeled anti-human IgG antibody (Chemicon, Catalog No. AP309P) diluted in PBST containing 5% skimmed milk powder was added, at 25° C. for 1 hour, and the plate was washed with PBST. Finally, colorimetric substrate TMB was used for color development, and the color was developed at room temperature for 10 minutes. 1M $H_2SO_4$ was added, the color development was terminated. The absorbance at 450 nm was read on the microplate reader.

Figure 12:
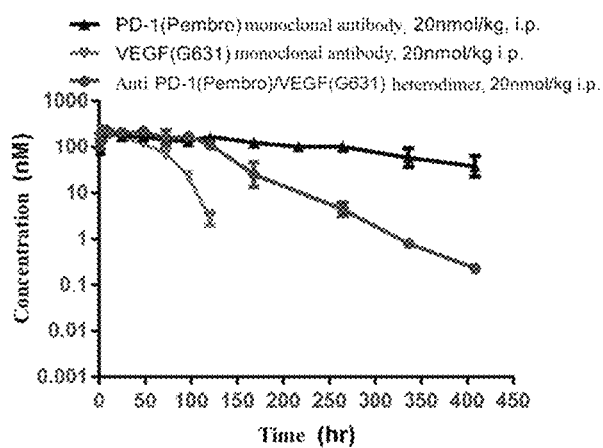
FIG. 12 shows the drug concentration-time curve of the anti-PD-1/VEGF heterodimeric antibody molecule.

The results are shown in FIG. 12, the pharmacokinetic characteristics of the anti-PD-1(Pembro)/VEGF(G631) heterodimeric antibody with a single intraperitoneal injection dose of 20 nmol/kg was better than the VEGF monoclonal antibody, but weaker than the PD-1 monoclonal antibody in mice. The pharmacokinetic parameters of the anti-PD-1 (Pembro)/VEGF(G631) heterodimeric antibody were as follows: the half-life $t_{1/2}$ was 35 hours; the area under the drug concentration-time curve $AUC_{last}$ was 25883 nM·hr; $C_{max}$ was 231 nM; the apparent volume of distribution Vd was 39 mL/Kg; the clearance rate CL was 0.77 mL/hr/kg; the mean residence time $MRT_{last}$ was 73 hours.

Example 10 Anti-Tumor Efficacy of Anti-PD-1/VEGF Heterodimeric Antibody in Mouse Tumor Model Human PD-1 knock-in mice (B6/JNju-hPDCD1em1Cin (E2E3)/Nju, Nanjing Biomedial Research Institute) on a C57BL/6 background, female, 6-8 weeks old, were selected as experimental materials. After one week of acclimatization to the environment, each mouse was subcutaneously inoculated with $5×10^6$ MC38 mouse colon cancer cells on the right back (Cell Centre of Basic Medical Sciences, Institute of Basic Medical Sciences, Chinese Academy of Medical Sciences). When the tumor volume grew to about 100 mm³, the mice were grouped according to the tumor volume, 6 tumor-bearing mice per group. The mice were administered with vehicle (PBS), a combination of the PD-1 (Pembro) monoclonal antibody 35 nmol/kg (5 mpk) and the VEGF (G631) monoclonal antibody 35 nmol/kg (5 mpk), and an anti-PD-1 (Pembro)/VEGF (G631) heterodimeric antibody 70 nmol/kg (10 mpk), twice a week for 2 consecutive weeks, and the administration method was intraperitoneal injection. From the day of administration, the tumor volume was measured 3 times a week, and the long axis a and short axis b were measured. The tumor volume calculation formula was: tumor volume (mm³)=(a×b²)/2. The duration of tumor volume measurement was 3 weeks, that is, after drug withdrawal, the observation was carried out for another week.

Figure 13:
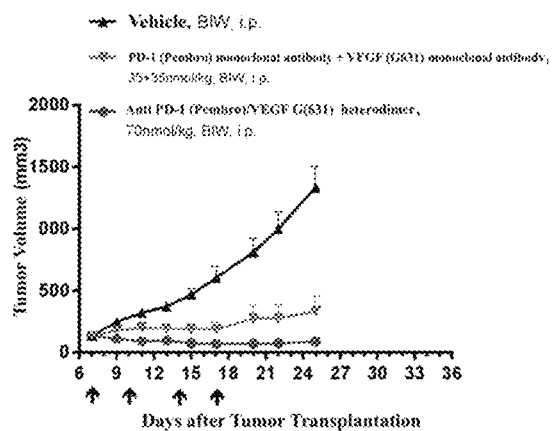
FIG. 13 shows the in vivo antitumor efficacy of the anti-PD-1/VEGF heterodimeric antibody molecule.

The results are shown in FIG. 13. Compared with the combination of the PD-1 monoclonal antibody and the VEGF monoclonal antibody, the anti-PD-1 (Pembro)/VEGF (G631) heterodimeric antibody had stronger anti-tumor efficacy, and it still showed good tumor control effects after drug withdrawal.

The invention claimed is:

1. A heterodimeric form bispecific antibody comprising a first antigen-binding functional region that is capable of specifically binding to PD-1 and a second antigen-binding functional region that is capable of specifically binding to VEGF, wherein the bispecific antibody comprises a first Fc chain and a second Fc chain with interchain-link through one or more disulfide bonds, the first Fc chain and the second Fc chain are respectively connected to the PD-1 antigen-binding functional region and the VEGF antigen-binding functional region through a covalent bond or a linker, alternatively, the first Fc chain and the second Fc chain are respectively connected to the VEGF antigen-binding functional region and the PD-1 antigen-binding functional region through a covalent bond or a linker; and the first Fc chain and the second Fc chain comprise 5 amino acid substitutions at the following positions:

amino acid substitutions at positions 366 and 399 on the first Fc chain, and amino acid substitutions at positions 351, 407, and 409 on the second Fc chain, the amino acid substitution is selected from the group consisting of:

a) substitutions T366L and D399R of the first Fc chain, and substitutions L351E, Y407L and K409V of the second Fc chain;

b) substitutions T366L and D399C of the first Fc chain, and substitutions L351G, Y407L and K409C of the second Fc chain;

c) substitutions T366L and D399C of the first Fc chain, and substitutions L351Y, Y407A and K409P of the second Fc chain;

d) substitutions T366P and D399N of the first Fc chain, and substitutions L351V, Y407P and K409S of the second Fc chain;

e) substitutions T366W and D399G of the first Fc chain, and substitutions L351D, Y407P and K409S of the second Fc chain;

f) substitutions T366P and D399I of the first Fc chain, and substitutions L351P, Y407F and K409F of the second Fc chain;

g) substitutions T366V and D399T of the first Fc chain, and substitutions L351K, Y407T and K409Q of the second Fc chain; and h) substitutions T366L and D399A of the first Fc chain, and substitutions L351W, Y407H and K409R of the second Fc chain; and amino acid positions are numbered according to Kabat EU index numbering system; and the first antigen-binding functional region comprises a VL set forth in SEQ ID NO: 10 and a VH set forth in SEQ ID NO: 12, or a VL set forth in SEQ ID NO: 16 and a VH set forth in SEQ ID NO: 18; and the second antigen-binding functional region comprises a VL set forth in SEQ ID NO: 2 and a VH set forth in SEQ ID NO: 6, or a VL set forth in SEQ ID NO: 8 and a VH set forth in SEQ ID NO: 22.

2. The heterodimeric form bispecific antibody according to claim 1, wherein the amino acid substitutions of the first Fc chain are T366L and D399R, and the amino acid substitutions of the second Fc chain are L351E, Y407L, and K409V.

3. The heterodimeric form bispecific antibody according to claim 1, wherein the Fc chain is derived from IgG.

4. The heterodimeric form bispecific antibody according to claim 1, wherein the PD-1 and VEGF antigen-binding functional regions are selected from a Fab fragment, a scFv fragment, a Fv fragment, and a VHH fragment.

5. The heterodimeric form bispecific antibody according to claim 1, wherein the PD-1 and VEGF antigen-binding functional regions are both Fab fragments.

6. The heterodimeric form bispecific antibody according to claim 1, wherein one of the PD-1 and VEGF antigen-binding functional regions is a Fab fragment and the other is an scFv.

7. The heterodimeric form bispecific antibody according to claim 5, wherein one of the Fab fragments comprises a first heavy chain variable region and a different second heavy chain variable region, and the other Fab fragment comprises a first light chain variable region and a different second light chain variable region.

8. The heterodimeric form bispecific antibody according to claim 1, wherein, when each of the first Fc chain covalently bonded to the PD-1 antigen binding region and the second Fc chain covalently bonded to the VEGF antigen binding region, or each of the first Fc chain covalently bonded to the VEGF antigen binding region and the second Fc chain covalently bonded to the PD-1 antigen binding region, is present alone in the presence of a reducing agent, the weight ratio of constituent homodimers is less than 50%.

9. The heterodimeric form bispecific antibody according to claim 1, wherein amino acid sequences of the bispecific antibody is selected from SEQ ID NOs: 2, 4, 6, 8, 10, 12, 14, 16, 18, 20, and 22.

10. An isolated polynucleotide encoding the heterodimeric form bispecific antibody according to claim 1.

11. A recombinant expression vector comprising the isolated polynucleotide according to claim 10.

12. The recombinant expression vector according to claim 11, wherein the recombinant expression vector is a plasmid vector XOGC engineered based on pcDNA.

13. A host cell comprising the isolated polynucleotide according to claim 10.

14. The host cell according to claim 13, which is selected from human embryonic kidney cell HEK293, or HEK293T, HEK293E, HEK293F engineered based on HEK293 cell; hamster ovary cell CHO, or CHO-S, CHO-dhfr, CHO/DG44, ExpiCHO engineered based on CHO cell; E. coli, or E. coli BL21, BL21(DE3), Rosetta, Origami engineered based on E. coli; a yeast, or Pichia pastoris, Saccharomyces cerevisiae, Kluyveromyces lactis, Hansenula polymorpha engineered based on yeast; an insect cell, or cells High5, SF9 engineered based on an insect cell; a plant cell; a mammary gland cell and a somatic cell of a mammal.

15. A composition comprising the heterodimeric form bispecific antibody according to claim 1, and a pharmaceutically acceptable carrier.

16. A method of producing the heterodimeric form bispecific antibody according to claim 1, comprising the steps of:
1) Expressing an isolated polynucleotide encoding the heterodimeric form bispecific antibody in host cells;
2) reducing the protein expressed in the host cells; and
3) mixing the reduced protein and then oxidizing the mixture.

17. The method according to claim 16, wherein the host cell is selected from human embryonic kidney cell HEK293, or HEK293T, HEK293F, HEK293F engineered based on HEK293 cell; hamster ovary cell CHO, or CHO-S, CHO-dhfr⁻, CHO/DG44, ExpiCHO engineered based on CHO cell; *E. coli*, or *E. coli* BL21, BL21(DE3), Rosetta, Origami engineered based on *E. coli*; a yeast, or *Pichia pastoris, Saccharomyces cerevisiae, Kluyveromyces lactis, Hansenula polymorpha* engineered based on yeast; an insect cell, or cells High5, SF9 engineered based on an insect cell; a plant cell; a mammary gland cell and a somatic cell of a mammal.

18. The method according to claim 16, wherein the reduction step comprises 1) performing a reduction reaction in the presence of a reducing agent selected from: 2-mercaptoethylamine, dithiothreitol, tris(2-carboxyethyl)phosphine or other chemical derivatives; and 2) removing the reduction agent.

19. The method according to claim 16, wherein the oxidizing step is oxidizing in air, and also includes performing an oxidation reaction in the presence of an oxidizing agent selected from: L-dehydroascorbic acid or its chemical derivatives.

20. The method according to claim 16, further comprising a step of separation and purification.

21. A method of preventing and/or treating a disease comprising administering the heterodimeric form bispecific antibody according to claim 1 to a subject in need thereof.

22. The method according to claim 21, wherein the subject is a mammal, preferably, a human subject.

23. The method according to claim 21, wherein the disease is selected from the following tumors: leukemia, lymphoma, myeloma, brain tumors, squamous cell carcinoma of the head and neck, non-small cell lung cancer, nasopharyngeal cancer, esophageal cancer, gastric cancer, pancreatic cancer, gallbladder cancer, liver cancer, colorectal cancer, breast cancer, ovarian cancer, cervical cancer, endometrial cancer, uterine sarcoma, prostate cancer, bladder cancer, renal cell carcinoma, melanoma.

24. The heterodimeric form bispecific antibody according to claim 1, wherein the amino acid substitution comprises substitutions T366L and D99C of the first Fc chain, and substitutions L351G, Y407L and K409C of the second Fc chain.

* * * * *